(12) United States Patent
Yin et al.

(10) Patent No.: US 7,071,342 B2
(45) Date of Patent: Jul. 4, 2006

(54) SYNTHESIS OF 2-HYDROXY-N,N-DIMETHYL-3-[ [2-[1(R)-(5-METHYL-2-FURANYL)PROPYL]AMINO]-3,4-DIOXO-1-CYCLOBUTEN-1-YL]AMINOBENZAMIDE

(75) Inventors: Jianguo Yin, Edison, NJ (US); Xiaoyong Fu, Edison, NJ (US); Shuyi Zhang, Parsippany, NJ (US); Timothy L. McAllister, Westfield, NJ (US); Agnes S. Kim-Meade, Fanwood, NJ (US); Jason L. Winters, East Windsor, NJ (US); Anantha Sudhakar, East Brunswick, NJ (US); Doris P. Schumacher, Bedminster, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/826,456

(22) Filed: Apr. 16, 2004

(65) Prior Publication Data

US 2004/0209946 A1    Oct. 21, 2004

Related U.S. Application Data

(60) Provisional application No. 60/463,773, filed on Apr. 18, 2003.

(51) Int. Cl.
C07D 307/54    (2006.01)
(52) U.S. Cl. .................................... 549/494
(58) Field of Classification Search ............... 549/494
See application file for complete search history.

(56) References Cited

FOREIGN PATENT DOCUMENTS

| GB | 2 298 861 A | 9/1996 |
|---|---|---|
| WO | WO 99/44985 | 9/1999 |
| WO | WO 02/083624 A1 | 10/2002 |
| WO | WO 03/080053 A1 | 10/2003 |
| WO | WO 2004/011418 A1 | 2/2004 |

OTHER PUBLICATIONS

Miao et al, Tet. Letters, 34(14), p. 2259-2262 (1993).*
Chakraborty, T.K., et al., "Diastereoselective Strecker Synthesis using α-Phenylglycinol as Chiral Auxiliary," *Tetrahedron Letters* 32(51):7597-7600 (1991).
Rampino, Louis D., et al., "Applicability of Palladium Synthetic High Polymer Catalysts," *J. Am. Chem. Soc.* 63:3268 (1941).
PCT Communication Relating to the Results of the Partial International Search for corresponding PCT Application No. PCT/US2004/011882.
Abstract No. 116:182817 and 1991-159963 for Japanese 3-95144 which is also submitted herewith.
PCT/US2004/011882, PCT International Preliminary Report on Patentability, Mar. 22, 2005.

Higashiyama, Kimio et al.., "Diastereoselective Addition of Organometallic . . . " Tetrahedron Letters, 33, No. 2: 235-238 (1992).
Chemical Abstract 130:153574 "Preparation of (benzoylamino) . . . " (for JP 11-29540 which is attached to said abstract).

* cited by examiner

*Primary Examiner*—Bernard Dentz
(74) *Attorney, Agent, or Firm*—Henry Jeanette; H. Eric Fischer

(57) ABSTRACT

Disclosed is a process for making the compound of formula I:

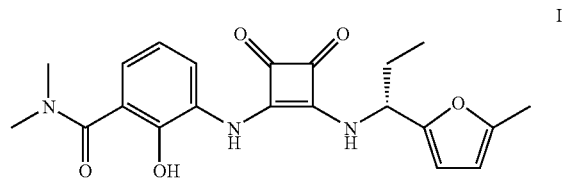

using the compounds of formulas II, Q, and XI or XII:

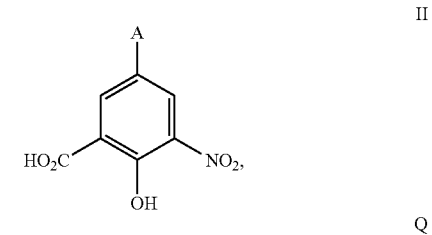

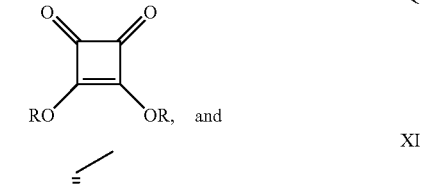

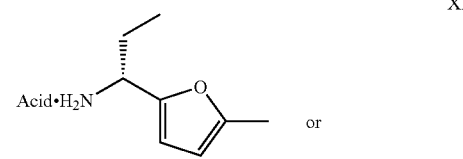

wherein A is selected from the group consisting of Br, Cl and I (with Br being preferred); and R represents $(C_1-C_{10})$alkyl. Also disclosed are intermediate compounds that are made in the disclosed process.

59 Claims, No Drawings

SYNTHESIS OF 2-HYDROXY-N,N-DIMETHYL-3-[ [2-[1(R)-(5-METHYL-2-FURANYL)PROPYL]AMINO]-3,4-DIOXO-1-CYCLOBUTEN-1-YL] AMINOBENZAMIDE

REFERENCE TO RELATED APPLICATION

This application claims the benefit of U.S. Provisional Application Ser. No. 60/463,773 filed Apr. 18, 2003, the disclosure of which is incorporated herein by reference thereto.

FIELD OF THE INVENTION

This application discloses a novel process to synthesize 2-Hydroxy-N,N-dimethyl-3-[[2-[[1(R)-(5-methyl-2-furanyl)propyl]amino]-3,4-dioxo-1-cyclobuten-1-yl]amino]benzamide.

BACKGROUND OF THE INVENTION

2-Hydroxy-N,N-dimethyl-3-[[2-[[1(R)-(5-methyl-2-furanyl)propyl]amino]-3,4-dioxo-1-cyclobuten-1-yl]amino]benzamide (compound of formula I):

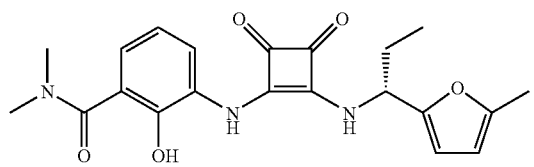

is disclosed in U.S. application Ser. No. 10/122,841 (filed Apr. 15, 2002 and now abandoned), Ser. No. 10/208,412 (filed Jul. 30, 2002), and Ser. No. 10/241,326 (filed Sep. 11, 2002), the disclosures of each being incorporated herein by reference thereto. The compound of formula I is also disclosed in WO 02/083624 (filed Apr. 15, 2002 and published Oct. 24, 2002).

The compound of formula I is useful for treating CXC chemokine-mediated diseases. Chemokines are chemotactic cytokines that are released by a wide variety of cells to attract macrophages, T-cells, eosinophils, basophils, neutrophils and endothelial cells to sites of inflammation and tumor growth. The CXC-chemokines include interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4.

There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding.

In view of the importance of antagonists that bind to the CXC-chemokine receptor novel methods of making such antagonists are always of interest.

SUMMARY OF THE INVENTION

This invention is directed to a process for making the compound of formula I:

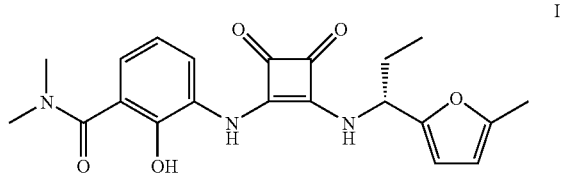

using the compounds of formulas II, Q, and XI or XII:

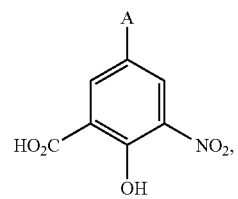

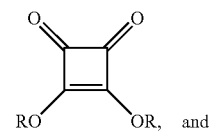

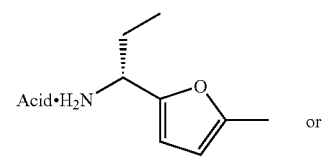

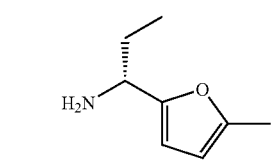

wherein A is selected from the group consisting of Br, Cl and I (with Br being preferred); and R represents $(C_1–C_{10})$alkyl.

This invention is also directed to a process for making a compound of formula V:

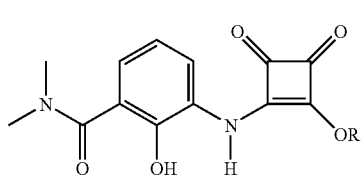

using compounds of the formulas II and Q:

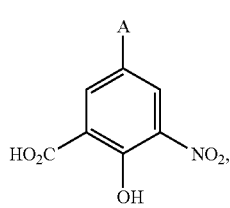

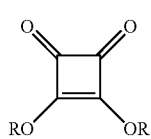

wherein A is selected from the group consisting of Br, Cl and I (with Br being preferred); and R represents $(C_1-C_{10})$alkyl.

This invention is also directed at making a compound of formula XI or XII:

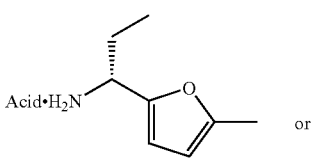

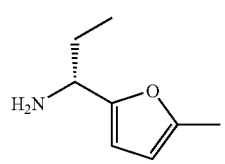

using a compound of formula III:

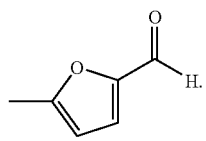

This invention is also directed to a process for making a compound of formula IV

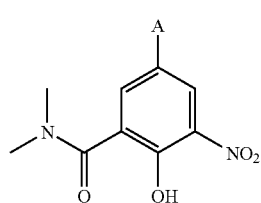

using a compound of formula II:

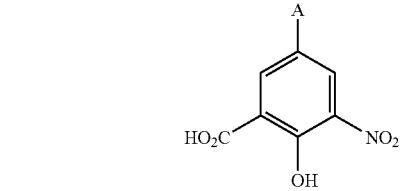

wherein A is selected from the group consisting of Br, Cl and I (with Br being preferred).

This invention is also directed to a process for making a compound of formula IV(i):

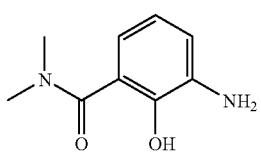

from a compound of formula II:

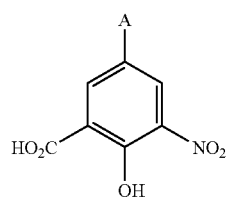

wherein A is selected from the group consisting of Br, Cl and I (with Br being preferred).

This invention is also directed to a process for making a compound of formula XIII:

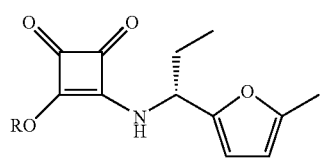

using compounds of the formulas Q and XI, or Q and XII:

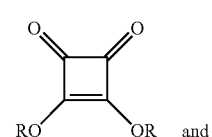

and

-continued

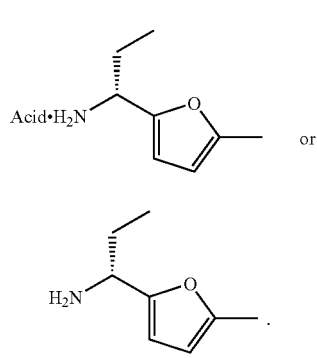

This invention is also directed to the intermediate compound

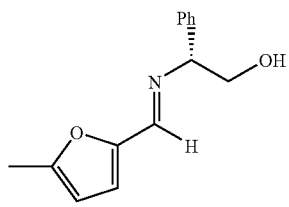

made during a process of this invention.

This invention is also directed to the intermediate compound

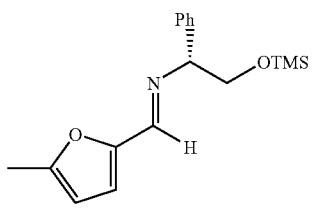

made during a process of this invention.

This invention is also directed to the intermediate compound

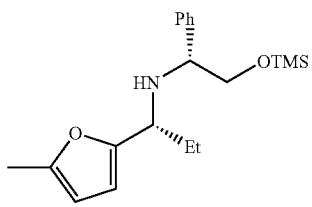

made during a process of this invention.

This invention is also directed to the intermediate compound

XI

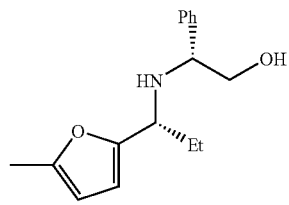

XII made during a process of this invention.

This invention is also directed to the intermediate compound

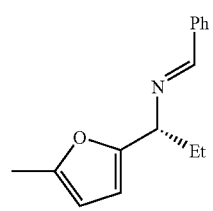

made during a process of this invention.

This invention is also directed to the intermediate compound

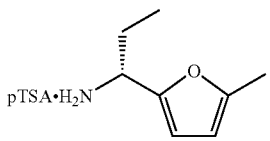

made during a process of this invention.

This invention is also directed to the intermediate compound

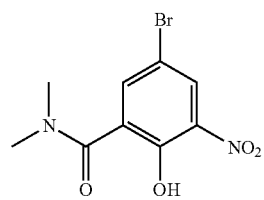

made during a process of this invention.

This invention is also directed to the intermediate compound

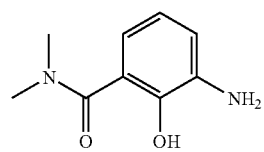

made during a process of this invention.

The inventive process to make the compound of formula I has several advantages: 5-bromo-3-nitrosalicylic acid is readily available and less expensive, there is no need to isolate the unstable reduction intermediate compound of formula IV(i), the compound of formula XI is more easily purified because no column chromatography is involved, and the salt formation of compound XI improved chiral purity of the amine.

DESCRIPTION OF THE INVENTION

As used herein, the following terms, unless otherwise indicated, have the following meanings:
"g"=grams.
"HPLC"=High Performance Liquid Chromatography.
"DBU"=1,8-diazabicyclo[5.4.0]undec-7-ene.
"DMAP"=4-dimethylaminopyridine.
"DME"=dimethylether.
"DMF"=N,N-dimethylformamide.
"DMSO"=dimethylsulfonic acid.
"MHz"=Megahertz.
"mL"=milliliters.
"Mp"=melting point.
"NMR"=nuclear magnetic resonance spectroscopy.
"THF"=tetrahydrofuran.
"TMS"=trimethylsilyl.
"TMSOTF"=trimethylsilyl-O-triflate.
"TBME"=T-butylmethyl ether.

"Alkyl" means an aliphatic hydrocarbon group, which may be straight or branched, and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group is substituted by one or more substituents each independently selected from the group consisting of: halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond, which may be straight or branched, and comprising about 2 to about 15 carbon atoms in the chain. Preferred alkenyl groups have about 2 to about 12 carbon atoms in the chain, and more preferably about 2 to about 6 carbon atoms in the chain. Branched means that one or more lower alkyl groups, such as methyl, ethyl or propyl, are attached to a linear alkenyl chain. "Lower alkenyl" means about 2 to about 6 carbon atoms in the chain, which may be straight or branched. The term "substituted alkenyl" means that the alkenyl group is substituted by one or more substituents each independently selected from the group consisting of: halo, alkyl, aryl, cycloalkyl, cyano, and alkoxy. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond, which may be straight or branched, and comprising about 2 to about 15 carbon atoms in the chain. Preferred alkynyl groups have about 2 to about 12 carbon atoms in the chain, and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain, which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group is substituted by one or more substituents each independently selected from the group consisting of: alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents", which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents", which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Ring system substituent" means a substituent attached to an aromatic or non-aromatic ring system, which, for example, replaces an available hydrogen on the ring system. Ring system substituents are each independently selected from the group consisting of: aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ are each independently selected from the group consisting of hydrogen, alkyl, aryl, and aralkyl.

"Cycloalkenyl" means a non-aromatic mono or multicyclic ring system comprising about 3 to about 10 carbon atoms, preferably about 5 to about 10 carbon atoms, which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means a heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen are replaced by an alkyl group as defined above.

"Arylamino" means an —$NH_2$ or —$NH_3^+$ group in which one or more of the hydrogen atoms on the nitrogen are replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S($O_2$)— group. The bond to the parent moiety is through the sulfonyl.

"Arylsulfinyl" means an aryl-S(O)— group. The bond to the parent moiety is through the sulfinyl.

"Suitable temperature" means the temperature which results in a desirable rate of a reaction, and usually it is the temperature that results in an acceptable yield of the desired product with the minimum production of undesirable products; or a "suitable temperature" is that temperature at which reagents can be safely mixed together, or that temperature at which a reaction mixture can be safely controlled, or that temperature at which the desired products are isolated from solution.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Non-limiting examples of suitable solvates include ethanolates, methanolates, and the like. "Hydrate" is a solvate wherein the solvent molecule is $H_2O$.

The embodiments described below are numbered for purposes of reference only.

The reagents and reaction conditions used, as described below, to make a particular compound in a particular step in the process for making the compound of formula I, are also applicable to any embodiment directed to a process for making that particular compound.

Embodiment No. 1 of this invention is directed to a process for making the compound of formula I:

I comprising:
(a) converting the compound of formula II

II to a compound of formula IV:

IV wherein A, in compounds of formulas II and IV, is selected from the group consisting of Br, Cl and I (preferably Br);

(b) hydrogenating the compound of formula IV with a suitable hydrogenation catalyst under hydrogen pressure, to form the intermediate compound of formula IV(i):

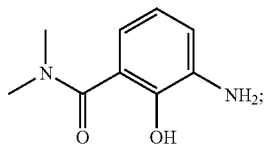

IV(i)

(c) reacting the compound of formula IV(i) with a compound of formula Q:

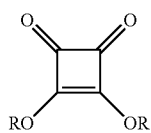

Q wherein R represents $(C_1-C_{10})$alkyl, to yield a compound of formula V:

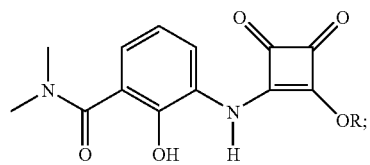

V (d) converting the compound of formula III

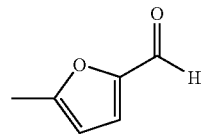

III to a compound of formula VI:

VI (e) adding a protecting group to the compound of formula VI to yield a compound of formula VII:

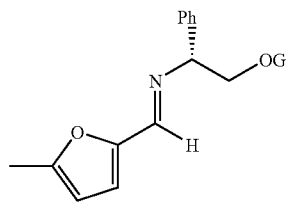

VII wherein G represents a protecting group;

(f) reacting the compound of formula VII with a suitable organometallic reagent, followed by work-up, to yield a compound of formula VIII:

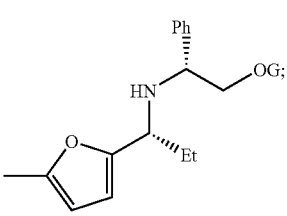

VIII (g) removing the protecting group (G) from the compound of formula VIII to yield a compound of formula IX:

IX (h) converting the compound of formula IX into an imine intermediate compound of formula X:

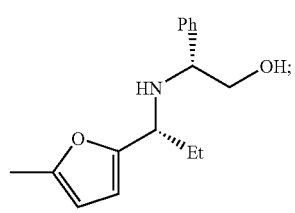

X (i) converting the imine intermediate compound of formula X into the salt of formula XI:

(j) reacting the compound of formula XI with the compound of formula V to yield the compound of formula I; or (k) converting the compound of formula XI to the free amine:

XII and reacting the compound of formula XII with the compound of formula V to yield the compound of formula I.

Those skilled in the art will appreciate that in the process of Embodiment No. 1, the order of making the compound of formula V and the compound of formula XI is not critical. Also the order of making the compound of formula V and the compound of formula XII is not critical.

Embodiment No. 2 of this invention is directed to a process for making the compound of formula I:

I comprising:
(a) converting the compound of formula III

III to a compound of formula VI:

VI (b) adding a protecting group to the compound of formula VI to yield a compound of formula VII:

VII wherein G represents a protecting group;

(c) reacting the compound of formula VII with a suitable organometallic reagent, followed by work-up, to yield a compound of formula VIII:

VIII (d) removing the protecting group (G) from the compound of formula VIII to yield a compound of formula IX:

IX (e) converting the compound of formula IX into an imine intermediate compound of formula X:

X (f) converting the imine intermediate compound of formula X into the salt of formula XI:

XI (g) reacting the compound of formula XI with the compound of formula Q:

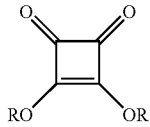

to yield a compound of formula XIII:

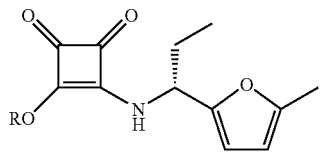

wherein R represents (C$_1$–C$_{10}$)alkyl in formulas Q and XIII; or (h) converting the compound of formula XI to a compound of formula XII:

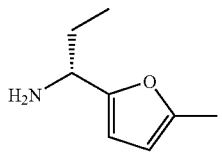

and reacting the compound of formula XII with a compound of formula Q:

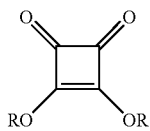

to yield a compound of formula XIII:

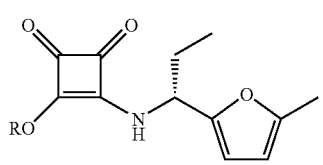

wherein R represents (C$_1$–C$_{10}$)alkyl in formulas Q and XIII;

(i) converting the compound of formula II

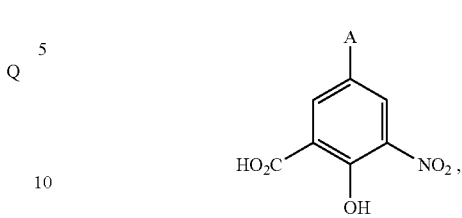

wherein A is selected from the group consisting of Br, Cl and I (preferably Br), to a compound of formula IV:

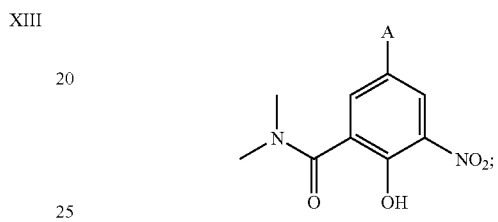

(j) hydrogenating the compound of formula IV with a suitable hydrogenation catalyst under hydrogen pressure, to form the intermediate compound of formula IV(i):

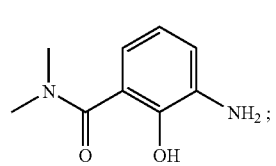

(k) reacting the compound of formula IV(i) with the compound of formula XIII to yield the compound of formula I.

Those skilled in the art will appreciate that in the process of Embodiment No. 2, the order of making the compound of formula XIII and the compound of formula IV(i) is not critical.

The reagents and reaction conditions used to make the compound of formula XI from the compound of formula III in steps (a) to (f) in Embodiment No. 2 are the same as those used to make the compound of formula XI from the compound of formula III in steps (d) to (i) in Embodiment No. 1.

The reagents and reaction conditions to convert the salt of formula XI to the free amine of formula XII in step (h) of Embodiment No. 2 are the same as those used to convert the salt of formula XI to the free amine of formula XII in step (k) of Embodiment No. 1.

The reagents and reaction conditions to make the compound of formula XIII from the compound of formula XI in step (g) of Embodiment No. 2 are the same as those used to make the compound of formula I, from the compounds of formulas V and XI, in step (j) of Embodiment No. 1.

The reagents and reaction conditions to make the compound of formula XIII from the compound of formula XII in step (h) of Embodiment No. 2 are the same as those used to make the compound of formula I, from the compounds of formula V and XII, in step (k) of Embodiment No. 1.

Embodiment No. 3 is directed to the process described in Embodiment No. 1 wherein the compound of formula XI is reacted with the compound of formula V to yield the compound of formula I.

Embodiment No. 4 is directed to the process described in Embodiment No. 1 wherein the compound of formula XI is converted to the free amine of formula XII, and said compound of formula XII is reacted with the compound of formula V to yield the compound of formula I.

Embodiment No. 5 is directed to the process described in Embodiment No. 2 wherein the compound of formula XI is reacted with the compound of formula Q to yield the compound of formula XIII.

Embodiment No. 6 is directed to the process described in Embodiment No. 2 wherein the compound of formula XI is converted to the free amine of formula XII, and said compound of formula XII is reacted with the compound of formula Q to yield the compound of formula XIII.

Embodiment No. 7 is directed to a process for making a compound of formula V:

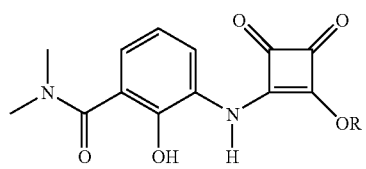

using compounds of the formulas II and Q:

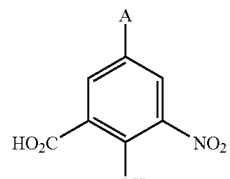

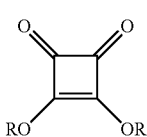

wherein A is selected from the group consisting of Br, Cl and I (with Br being preferred); and R represents $(C_1-C_{10})$alkyl. The reagents and reaction conditions used in this embodiment are the same as those used in the preparation of the compound of formula V from compounds of formulas II and Q described in Embodiment No. 1 steps (a) to (c).

Embodiment No. 8 is directed to a process for making a compound of formula XI or XII:

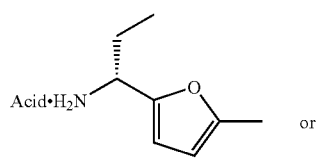

or

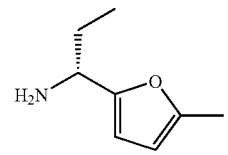

using a compound of formula III:

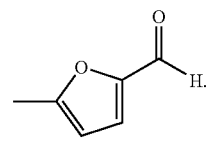

The reagents and reaction conditions used in this embodiment are the same as those used in the preparation of the compound of formula XI or XII from compound of formula III described in Embodiment No. 1 steps (d) to (i), and, for XII, the conversion step in step (k).

Embodiment No. 9 is directed to a process for making a compound of formula IV

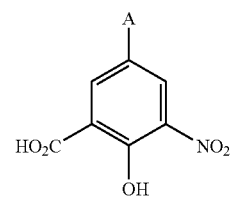

using a compound of formula II:

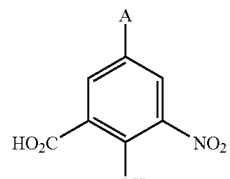

wherein A is selected from the group consisting of Br, Cl and I (with Br being preferred). The reagents and reaction conditions used in this embodiment are the same as those used in the preparation of the compound of formula IV from compound of formula II described in Embodiment No. 1 step (a).

Embodiment No. 10 is directed to a process for making a compound of formula IV(i):

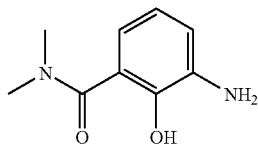

from a compound of formula II:

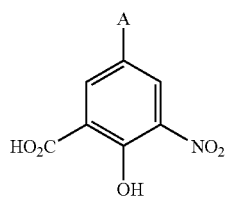

wherein A is selected from the group consisting of Br, Cl and I (with Br being preferred). The reagents and reaction conditions used in this embodiment are the same as those used in the preparation of the compound of formula IV(i) from compound of formula II described in Embodiment No. 1 steps (a) and (b).

Embodiment No. 11 is directed to a process for making a compound of formula XIII:

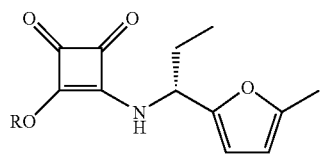

using compounds of the formulas Q and XI, or Q and XII:

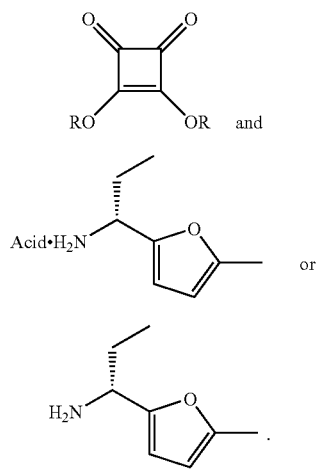

The reagents and reaction conditions used in this embodiment are the same as those used in the preparation of the compound of formula XIII from compounds of formulas Q and XI, or Q and XII, described in Embodiment No. 2 steps (a) to (h).

Embodiment No. 12 is directed to a process for preparing a compound of formula I:

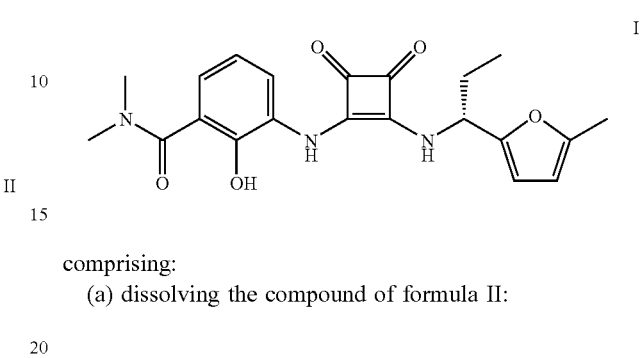

comprising:
(a) dissolving the compound of formula II:

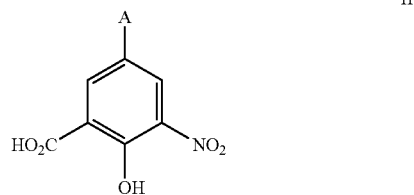

in:
a solvent selected from the group consisting of: acetonitrile, THF, t-butylmethylether, methylenechloride, toluene, ethylacetate, diethylether, and chloroform, and an acid chloride selected from the group consisting of: thionyl chloride and oxalyl chloride, wherein a catalytic amount of DMF is optionally used when oxalyl chloride is used;

and adjusting the temperature of the resulting reaction mixture to a about −20° C. to about 110° C.;

cooling the reaction mixture, when the reaction is complete, to a temperature of about 5° C. to about 10° C.;

adding dimethylamine gas or a solution of dimethylamine, at a concentration of at least about 1 molar equivalent with respect to the compound of formula II, wherein the solvent for said dimethylamine solution is selected from the group consisting of: acetonitrile, THF, t-butylmethylether, methylenechloride, toluene, ethylacetate, diethylether, and chloroform;

adjusting the temperature of the resulting reaction mixture to a temperature of about −20° C. to about 50° C.;

acidifying the resulting reaction mixture with an aqueous acid to a pH of about 0 to about 7, to produce a compound of formula IV:

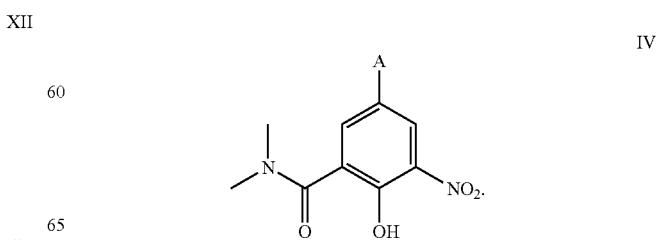

wherein A is in the compounds of formulas II and IV is selected from the group consisting of Br, Cl and I;

(b) hydrogenating the compound of formula IV by mixing said compound of formula IV with:

a base selected from the group consisting of: KOH, NaOH, Na₂CO₃, K₂CO₃, K₂CO₃, NaHCO₃, KHCO₃, tetramethylguanidine, DBU, diisopropylethylamine and mixtures thereof, wherein said base is in a concentration of at least about 1 molar equivalent with respect to the compound of formula IV, a hydrogenation catalyst selected from the group consisting of: Pd/C, Pt/C, PdOH, and Raney nickel; and a solvent selected from the group consisting of: THF, methanol, ethanol, propanol, isopropanol, acetonitrile, ethyl acetate, and mixtures thereof; and pressurizing the resulting mixture under hydrogen at a pressure of about 10 to about 500 psi to produce the intermediate compound of formula IV(i):

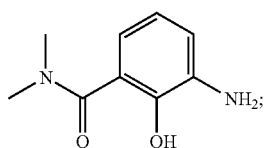

(c) adding the compound of formula Q:

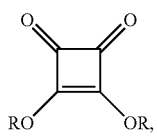

in a concentration of at least 1 molar equivalent with respect to the compound of formula IV(i), to the reaction mixture comprising the compound of formula IV(i) obtained in step (b), and adjusting the temperature to about 0° C. to about 80° C. to produce a compound of formula V:

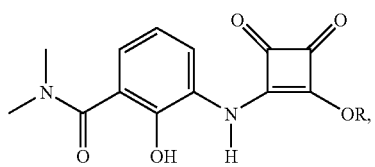

wherein R in said compound of formula Q is selected from the group consisting of: methyl, ethyl, propyl and isopropyl, and wherein said reaction is optionally catalyzed by a base selected from the group consisting of: KOH, NaOH, Na₂CO₃, K₂CO₃, NaHCO₃, KHCO₃, tetramethylguanidine, DBU, diisopropylethylamine, and mixtures thereof;

(d1) mixing: the compound of formula V from step (c) with the compound of formula XI

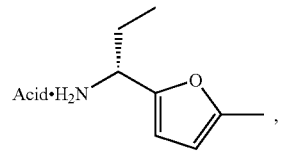

and a base in a solvent, heating the resulting reaction mixture to a temperature of about 20° C. to about 150° C., and then acidifying the reaction mixture to a pH of about 3 to about 7, to produce a compound of formula I; said base being selected from the group consisting of: pyridine, dimethylaminopyridine (DMAP), diisopropylethylamine and —N(R²)₃; wherein each R² is independently selected from the group consisting of: alkyl and cycloalkyl; and said base being used in a concentration of at least about 1 molar equivalent with respect to the compound of formula IV; and said solvent being selected from the group consisting of: nitrile, ether, and alcohol solvents; or (d2) mixing the compound of formula XI:

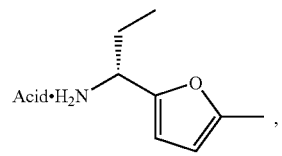

with water and solvent selected from the group consisting of: ethers and methylene chloride;

basifying the resulting reaction mixture with a base selected from the group consisting of: NaOH, KOH, Mg(OH)₂, Na₂CO₃ and K₂CO₃, to a pH of about 7 to about 14, said basification being done at a temperature of about 0° C. to about 50° C. to produce a compound of formula XII:

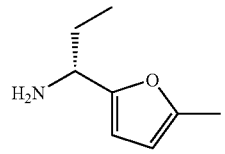

dissolving said compound of formula V from step (c) in a solvent selected from the group consisting of: alcohol solvents, nitrile solvents, ether solvents and toluene;

mixing the resulting solution with the compound of formula XII, and optionally adding a catalytic amount of a base to the resulting solution, wherein said base is selected from the group consisting of: pyridine and —N(R³)₃, wherein R³ is selected from the group consisting of: alkyl, aryl, aralkyl, and arylalkyl, and wherein the temperature of the resulting solution is about 10° C. to about 150° C., to produce a compound of formula I;

(e) wherein said compound of formula XI is prepared by:
mixing the compound of formula III:

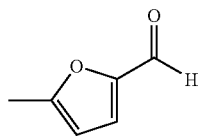

III with 0.01 molar equivalent, with respect to the compound of formula III, of R-2-(−)-phenylglycinol in a solvent selected from the group consisting of: aromatic solvents, halogenated solvents, alcohol solvents, nitrile solvents, ether solvents, and mixtures thereof, and heating the resulting mixture at reflux to produce a compound of formula VI:

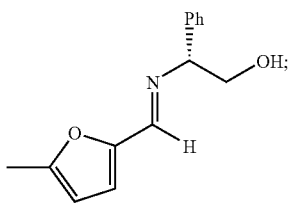

VI mixing the solution comprising the compound of formula VI with a silylating reagent selected from the group consisting of: hexamethyldisilazane, TMS chloride, and TMSOTF, wherein the TMS chloride or TMSOTF is used in combination with an aryl or alkyl base, and an acid in a concentration of at least about 0.2 molar equivalent with respect to the compound of formula VI, preferably at least about 0.4 molar equivalents, said acid being selected from the group consisting of: ammonium sulphate, ammonium nitrate, ammonium chloride, $H_2SO_4$, HCl, $H_3PO_4$, citric acid, mesyl chloride, paratoluenesulfonic acid, paratoluenesulfonic acid pyridinium salt, and alkylsulfonic acid, and heating the resulting reaction mixture at reflux to produce an imine compound of formula VII:

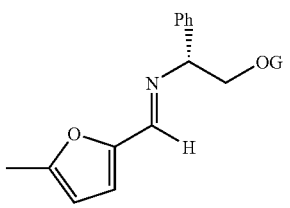

VII wherein G represents a protecting group that is the silylating reagent used;

mixing said imine compound of formula VII with an organometallic reagent in a solvent at a temperature of about 0° C. to about 80° C., said organometallic reagent being selected from the group consisting of: diethyl zinc, ethylzinc bromide, ethylzinc chloride, ethylmagnesium bromide, ethylmagnesium chloride and ethyllithium, said organometallic reagent being used in a concentration of 0.1 to about 5 molar equivalents with respect to the compound of formula VII, said solvent being selected from the group consisting of: benzene, toluene, TBME, THF, DME, dimethoxyethane, and mixtures thereof, to produce a compound of formula VIII:

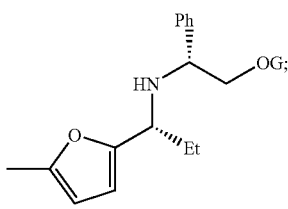

VIII adding the compound of formula VIII to a cooled aqueous acid, said acid being at a concentration of about 2.5 to about 5 molar equivalents with respect to the compound of formula VIII, adding water and a cosolvent and mixing the resulting mixture, adding a base to said mixture to adjust the pH of the aqueous phase to about 9 to about 13, to produce a compound of formula IX:

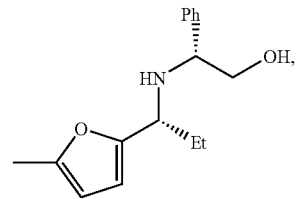

IX said co-solvent being selected from the group consisting of: methanol, ethanol, propanol, isopropanol, butanol, sec-butanol, pentanol, hexanol, heptanol, octanol, and mixtures thereof, said base being selected from the group consisting of: ammonium hydroxide, metal hydroxide, metal oxide, metal carbonate, metal bicarbonate, and mixtures thereof, wherein said metal is selected from the group consisting of: lithium, sodium, potassium, rubidium, cesium, beryllium, magnesium, calcium, strontium, barium, aluminum, indium, thallium, titanium, zirconium, cobalt, copper, silver, zinc cadmium, mercury and cerium, or said base being selected from the group consisting of: a metal salt of a $(C_1-C_{12})$alkanol and a $(C_3-C_{12})$cycloalkanol, wherein the metal is selected from the group consisting of: Li, Na, K, and Mg;

dissolving the compound of formula IX in solvent selected from the group consisting of: water, methanol, ethanol, propanol, isopropanol, butanol, sec-butanol, pentanol, hexanol, tetrahydrofuran, 1,2-dimethoxyethane, 1,2-diethoxymethane, diglyme, 1,4-dioxane, and mixtures thereof, cooling the resulting solution to a temperature of about −5° C. to about 20° C., adding $R^4NH_2$ to said solution, and then adding an agent selected from the group consisting of: NaIO$_4$, Pb(OAc)$_4$, H$_5$IO$_6$, and mixtures thereof, to produce a compound of X:

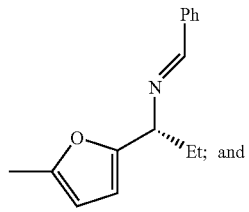

wherein R$^4$ is selected from the group consisting of alkyl, cycloalkyl, heterocycloalkyl, aryl, heteroaryl, and aralkyl;

dissolving the compound of formula X in a solvent and adding the resulting solution to an acid solution at a temperature ranging preferably from about −50° C. to about 80° C. to produce the compound of formula XI:

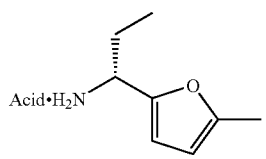

said compound XI being a salt, wherein said solvent is selected from the group consisting of: hydrocarbon solvents and ethers and mixtures thereof, and said acid is selected from the group consisting of: sulfonic acids, tartaric acids, H$_2$SO$_4$, HCl, H$_3$PO$_4$, HBr, carboxylic acids and mixtures thereof.

Embodiment No. 13 is directed to a process as described in Embodiment No. 12 except that:

in step (a), the preparation of the compound of formula IV, the reaction mixture of said compound of formula II and said acid chloride is 40° C. to about 90° C., said dimethylamine is at a concentration of at least about 2 molar equivalents with respect to the compound of formula II, said temperature of said reaction mixture is about 0° C. to about 25° C., said reaction mixture is acidified to a pH of about 1 to about 5, said acid for said aqueous acid is selected from the group consisting of: HCl, H$_2$SO$_4$, H$_3$PO$_4$, and mixtures thereof;

in step (b), the hydrogenation of the compound of formula IV, said base is selected from the group consisting of: Na$_2$CO$_3$, K$_2$CO$_3$, and mixtures thereof, said base is used at a concentration of about 1.05 to about 1.5 molar equivalents, said catalyst is selected from the group consisting of Pd/C and PdOH, said solvent is selected from the group consisting of: methanol, ethanol, propanol, isopropanol, and mixtures thereof, and said hydrogen pressure is about 20 to about 200 psi;

in step (c), the reaction of the compound of formula Q with the compound of formula IV(i), the compound of formula Q is used at a concentration of about 1 to about 2 molar equivalents, said temperature is about 20° C. to about 50° C., and said optional base is selected from the group consisting of: Na$_2$CO$_3$, K$_2$CO$_3$ and mixtures thereof;

in step (d1), the reaction of the compound of formula V with the compound of formula XI, said base is used in an amount of about 1 to about 2 molar equivalents with respect to the compound of formula V, said solvent is selected from the group consisting of alcohol and nitrile solvents, said temperature is about 40° C. to about 80° C., and said pH is about 3 to about 5;

in step (d2), the reaction of the compound of formula V with the compound of formula XII:
  said mixture with said compound of formula XI is basified with NaOH or KOH to a pH of about 10 to about 14 at a temperature of about 10° C. to about 40° C. to produce said compound of formula XII,
  said compound of formula V is dissolved an alcohol solvent,
  said compound of formula XII being used at a concentration about 1 molar equivalent with respect to the compound of formula V,
  said catalytic base being selected from the group consisting of: pyridine and —N(R$^3$)$_3$ wherein each R$^3$ is independently selected from the group consisting of ethyl, isopropyl, propyl, butyl, phenyl, tolyl and benzyl, and
  said temperature of said resulting solution with the compound of formula XII being about 40° C. to about 80° C.;

in step (e), in the reaction to produce the compound of formula VI from the compound of formula III, said R-2-(−)-phenylglycinol is in a concentration of about 0.5 to about 1.5 molar equivalents, and said solvent for said R-2-(−)-phenylglycinol is selected from the group consisting of: benzene, toluene, dichloromethane, methylene chloride, chlorobenzene, methanol, ethanol, propanol, isopropanol, n-propanol, butanol, acetonitrile, THF and t-butylmethylether;

in step (e) in the reaction to produce the compound of formula VII from the compound of formula VI, said silylating reagent is selected from the group consisting of: hexamethyldisilazane, TMS chloride, and TMSOTF, wherein the TMS chloride or TMSOTF is used in combination with triethylamine, and said acid is selected from the group consisting of: ammonium sulphate, ammonium nitrate and ammonium chloride, said acid at a concentration of at least about 0.4 molar equivalents with respect to the compound of formula VI;

in step (e), in the reaction to produce the compound of formula VIII from the compound of formula VII, said organometallic reagent is used in a concentration of about 1 to about 5 molar equivalents with respect to the compound of formula VII, said solvent is selected from the group consisting of: THF, TBME, and mixtures thereof, and said temperature is about 10° C. to about 50° C.;

in step (e), in the reaction to produce the compound of formula IX from the compound of formula VIII, said cooled aqueous acid is at a temperature of about 0° C. to about 15° C., said acid is selected from the group consisting of: H$_2$SO$_4$, HCl, H$_3$PO$_4$, and mixtures thereof, said acid is in a concentration of about 2.5 to about 3 molar equivalents with respect to the compound of formula VIII, said cosolvent is selected from the group consisting of: methanol, ethanol, propanol, isopropanol, butanol, sec-butanol, pentanol, hexanol, heptanol, octanol, and mixtures thereof, said base is selected from the group consisting of: KOH, NaOH, NH$_4$OH, LiOH and CsOH, and said pH is adjusted to about 10 to about 11, in step (e), in the reaction to produce the compound of formula X from the compound of formula IX, the resulting solution is cooled to about 0° C. to about 15° C., and said R$^4$ is a (C$_1$–C$_3$)alkyl; and in step (e), in the reaction to produce the compound of formula XI from the compound of formula X, said compound of formula XI is dissolved in a solvent selected from the group consisting of: toluene, xylene, chlorobenzene, dichlorobenzene, diethyl ether, dipropyl ether and dibutyl ether, 1,2-dimethoxyethane, 1,2-diethoxyethane, diglyme, 1,4-dioxane, tetrahydrofuran and mixtures thereof, said acid in said acid solution is selected from the group consisting of: paratoluene sulfonic acid and alkylsulfonic acids, and said temperature is about −20° C. to about 20° C.

Embodiment No. 14 is directed to a process as described in Embodiment No. 13 except that:

in step (a), the preparation of the compound of formula IV, said compound of formula II is dissolved in acetonitrile and thionyl chloride, said temperature is about 65° C. to about 75° C., said dimethylamine is dissolved in acetonitrile, said dimethylamine being at a concentration of about 2.5 molar equivalents with respect to the compound of formula II, said temperature of said reaction mixture is about 5° C. to about 10° C., said reaction mixture is acidified to a pH of about 2 to about 3, said aqueous acid is H$_2$SO$_4$, and said substituent A is Br;

in step (b), the hydrogenation of the compound of formula IV, said base is K$_2$CO$_3$ used at a concentration of about 1.05 to about 1.1 molar equivalents, said catalyst is Pd/C, said solvent is ethanol, and said hydrogen pressure is about 100 to about 120 psi;

in step (c), the reaction of the compound of formula Q with the compound of formula IV(i), the compound of formula Q is used at a concentration of about 1.3 to about 1.5 molar equivalents, said temperature is about 25° C. to about 35° C., R is ethyl, and said optional base is K$_2$CO$_3$;

in step (d1), the reaction of the compound of formula V with the compound of formula XI, the compound of formula XI is used in an amount of about 1.1 molar equivalents, said base is triethylamine used in an amount of about 1.3 to about 1.5 molar equivalents with respect to the compound of formula V, said solvent is acetonitrile, said temperature is about 60° C. to about 70° C., and said pH is about 4;

in step (d2), the reaction of the compound of formula V with the compound of formula XII, said solvent used with said compound of formula XI is t-butyl methyl ether, said mixture with said compound of formula XI is basified with NaOH to a pH of about 12.5 to about 13.5 at a temperature of about 20° C. to about 30° C. to produce said compound of formula XII, said compound of formula V is dissolved in the solvent n-propanol, said compound of formula XII being used at a concentration about 1.1 molar equivalents with respect to the compound of formula V, said catalytic base being diisopropylethylamine, said temperature of said resulting solution with the compound of formula XII being about 60° C. to about 70° C.

in step (e), in the reaction to produce the compound of formula VI from the compound of formula III, said R-2-(−)-phenylglycinol is in a concentration of about 0.9 to about 1.1 molar equivalents, and said solvent for said R-2-(−)-phenylglycinol is THF;

in step (e) in the reaction to produce the compound of formula VII from the compound of formula VI, said silylating reagent is hexamethyldisilazane, and said acid is ammonium sulphate at a concentration of at least about 0.5 molar equivalents with respect to the compound of formula VI;

in step (e), in the reaction to produce the compound of formula VIII from the compound of formula VII, said organometallic reagent is ethylmagnesium bromide used in a concentration of about 2 to about 3 molar equivalents with respect to the compound of formula VII, said solvent is TBME, and said temperature is about 20° C. to about 35° C.;

in step (e), in the reaction to produce the compound of formula IC from the compound of formula VIII, said cooled aqueous acid is at a temperature of about 0° C. to about 10° C., said acid is H$_2$SO$_4$, said acid is in a concentration of about 2.5 molar equivalents with respect to the compound of formula VIII, said cosolvent is sec-butanol, said base is NH$_4$OH, and said pH is adjusted to about 11, in step (e), in the reaction to produce the compound of formula X from the compound of formula IX, said compound of formula IX is dissolved in ethanol and the resulting solution is cooled to about 0° C. to about 10° C., said R$^4$ is methyl, and said agent is NaIO$_4$; and in step (e), in the reaction to produce the compound of formula XI from the compound of formula X, said compound of formula XI is dissolved in THF, said acid in said acid solution is paratoluene sulfonic acid, and said temperature is about 0° C. to about 10° C.

The protecting group G is selected from the group consisting of: silylating reagents and esters (i.e., moieties having the formula R$^1$—C(O)—O—). Suitable silylating reagents include hexamethyldisilazane, TMS chloride, TMSOTF, and the like, wherein the TMS chloride or TMSOTF is used in combination with an aryl or alkyl base. Preferred silylating agents include hexamethyldisilazane, TMS chloride, TMSOTF, wherein the TMS chloride or TMSOTF is used in combination with triethylamine. More preferably, the silylating agent is hexamethyldisilazane. R$^1$ is selected from the group consisting of: alkyl (e.g., methyl, ethyl and isopropyl), aryl (e.g., phenyl), and cycloalkyl (e.g., cyclopropyl and cyclohexyl). When and ester is used then diethyl zinc is used to produce the compound of formula VIII from the compound of formula VII. The ester protecting group can be removed by basic hydrolysis wherein the base is a metal hydroxide, such as, for example, NaOH, KOH, LiOH and Ba(OH)$_2$.

Compound XI is the (R)-isomer. Those skilled in the art will appreciate that if the (S)-isomer were to be used the other enantiomer of formula I would be obtained.

The processes of this invention (for example the processes of Embodiment Nos. 1, 3, 4, 7, 8, 9 and 10) are described in Schemes I and II below.

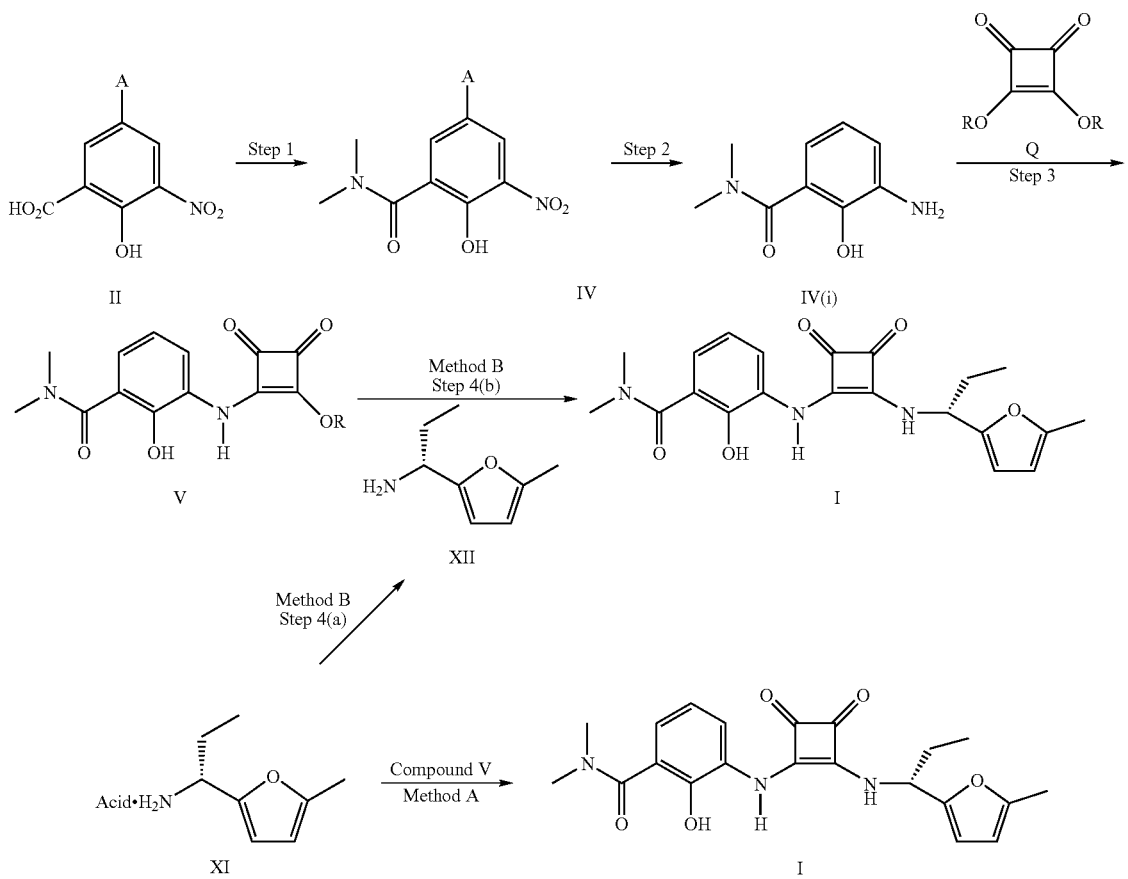

Step 1:

The compound of formula II is dissolved in a suitable solvent and a suitable acid chloride. Non-limiting examples of suitable solvents preferably include acetonitrile, THF, t-butylmethylether, methylenechloride, toluene, ethylacetate, diethylether, chloroform, and toluene, and more preferably acetonitrile. Non-limiting examples of suitable acid chlorides include thionyl chloride and oxalyl chloride, preferably thionyl chloride. If oxalyl chloride is used, a catalytic amount of DMF is also preferably used. The resulting mixture is stirred at a temperature ranging from about −20° C. to about 110° C., preferably from about 40° C. to about 90° C., most preferably from about 65° C. to about 75° C., for about 2 hours or until the reaction is complete. The range of temperatures above can vary depending on which solvent is used. The reaction mixture is then cooled to a temperature ranging from about 5° C. to about 10° C., and dimethylamine gas or a solution of dimethylamine in a suitable solvent is added slowly for over about one hour or until the reaction is complete. Non-limiting examples of suitable solvents which can be added to the dimethylamine include acetonitrile, THF, t-butylmethylether, methylenechloride, toluene, ethylacetate, diethylether, and chloroform, and preferably acetonitrile. The dimethylamine can be used generally at a concentration of at least about 1 molar equivalent with respect to the compound of formula II, preferably at least about 2 molar equivalents, and even more preferably about 2.5 molar equivalents. The reaction mixture is then adjusted to a temperature ranging from about −20° C. to about 50° C., preferably from about 0° C. to about 25° C., more preferably from about 5° C. to about 10° C., for about 3 hours or until the reaction is complete. The mixture is then acidified with an aqeous acid to a pH ranging from about 0 to about 7, preferably from about 1 to about 5, more preferably from about 2 to about 3. Non-limiting examples of aqeous acids include HCl, $H_2SO_4$ or $H_3PO_4$, and the like, or mixtures thereof, preferably HCl, $H_2SO_4$, or mixtures thereof, more preferably $H_2SO_4$. The product of step 1 is the compound of formula IV which can be purified preferably by crystallization.

Preparation of the Compound of Formula V

Step 2:

A mixture is prepared containing the compound of formula IV from step 1, a base, a hydrogenation catalyst, and a solvent. Non-limiting examples of suitable bases include KOH, NaOH, $Na_2CO_3$, $K_2CO_3$, $NaHCO_3$, $KHCO_3$, tetramethylguanidine, DBU, diisopropylethylamine, and the like, or mixtures thereof, more preferably $Na_2CO_3$, $K_2CO_3$, or mixtures thereof, most preferably $K_2CO_3$. Non-limiting examples of hydrogenation catalysts include Pd/C, Pt/C, PdOH, or Raney nickel, preferably Pd/C or PdOH, and more preferably Pd/C. Non-limiting examples of suitable solvents include THF, methanol, ethanol, propanol, isopropanol, acetonitrile, ethyl acetate, and the like, or mixtures thereof, preferably methanol, ethanol, propanol, isopropanol, or mixtures thereof, and more preferably ethanol. The base can be used generally in at least about 1 molar equivalent with respect to the compound of formula IV, preferably from about 1.05 to about 1.5 molar equivalents, and more preferably from about 1.05 to about 1.1 molar equivalents. The mixture is pressurized under hydrogen generally from about 10 to about 500 psi, preferably from about 20 to about 200 psi, and more preferably from about 100 to about 120 psi for about 10 hours, or until the reaction is complete to yield the intermediate compound of formula IV(i). The intermediate compound of formula IV(i) need not be isolated and can be used in the next step directly.

Step 3:

To the solution containing the compound of formula IV(i) from step 2 is added the compound of formula Q (3,4-dialkoxy-3-cyclobutene-1,2-dione), wherein R represents $(C_1-C_{10})$alkyl, preferably $(C_1-C_6)$alkyl, and even more preferably $(C_1-C_3)$alkyl (e.g., methyl, ethyl, propyl and isopropyl, and preferably ethyl). The compound of formula Q can be used generally in at least 1 molar equivalent with respect to the compound of formula IV(i), more preferably from about 1 to about 2 molar equivalents, most preferably from about 1.3 to about 1.5 molar equivalents. The solution is stirred at a temperature ranging from about 0° C. to about 80° C., preferably from about 20° C. to about 50° C., more preferably from about 25° C. to about 35° C., for about 2 hours, or until the reaction is complete to yield the compound of formula V. The reaction is preferably catalyzed by a base. Non-limiting examples of suitable bases include KOH, NaOH, $Na_2CO_3$, $K_2CO_3$, $K_2CO_3$, $NaHCO_3$, $KHCO_3$, tetramethylguanidine, DBU, diisopropylethylamine, and the like, or mixtures thereof. Preferred bases include $Na_2CO_3$, $K_2CO_3$, or mixtures thereof, more preferably $K_2CO_3$. To maximize the yield at the end of the reaction, the reaction mixture is acidified with a suitable acid to a pH of about 5 to about 6. Suitable acids include, for example, carboxylic acids (such as, for example, acetic acid and benzoic acid), and inorganic acids (such as, for example, $H_2SO_4$, HCl, and phosphoric acid), with acetic acid being preferred.

Preparation of the Compound of Formula I

Method A:

A mixture is prepared containing the compounds of formulae V from step 3 and XI, a base and a solvent. Non-limiting examples of suitable bases include pyridine, dimethylaminopyridine (DMAP), diisopropylethylamine, —$N(R^2)_3$, wherein each $R^2$, which can be the same or different, represents alkyl or cycloalkyl. Preferred bases include —$N(R^2)_3$, wherein each $R^2$ represents alkyl or cycloalkyl, such as, for example, triethylamine, tributylamine and the like. A more preferred base is triethylamine. Suitable solvents include nitrile (such as, for example, acetonitrile), ether (such as, for example, diethylether, THF, dibutylether, and t-butylmethylether), and alcohol solvents (such as, for example, methanol, ethanol, isopropanol, n-propanol, n-butanol, and sec-butanol), more preferably alcohol and nitrile solvents, and even more preferably acetonitrile. The compound of formula XI can be added in any molar ratio, preferably in about 1 molar equivalent with respect to the compound of formula V, more preferably in about 1.1 molar equivalents. The base can be used generally in at least about 1 molar equivalent with respect to the compound of formula IV, preferably from about 1 to about 2 molar equivalents, and more preferably from about 1.3 to about 1.5 molar equivalents. The mixture is heated to a temperature preferably ranging from about 20° C. to about 150° C., more preferably from about 40° C. to about 80° C., and even more preferably from about 60° C. to about 70° C. When the reaction is complete, the reaction mixture is acidified (with, for example, a carboxylic acid, such as, for example, acetic acid and benzoic acid, or an inorganic acid, such as, for example, $H_2SO_4$, HCl and phosphoric acid, with acetic acid being preferred) until the pH of the mixture is preferably from about 3 to about 7, more preferably from about 3 to about 5, and even more preferably about 4. The compound of formula I can be purified preferably upon crystallization.

Method B:

Step 4(a):

The compound of formula XI, is mixed in water and a suitable solvent. Non-limiting examples of suitable solvents include organic solvents such as ethers (such as, for example, diethylether, dibutyl ether and t-butyl methyl ether) and methylene chloride, preferably ethers, more preferably t-butyl methyl ether. The reaction mixture is basified in inorganic base at a temperature ranging preferably from about 0° C. to about 50° C., more preferably from about 10° C. to about 40° C., and even more preferably from about 20° C. to about 30° C. for about 20 minutes or until the reaction is complete. The reaction mixture is basified to a pH ranging preferably from about 7 to about 14, more preferably from about 10 to about 14, and even more preferably from about 12.5 to about 13.5. Non-limiting examples of suitable bases include inorganic bases such as NaOH, KOH, $Mg(OH)_2$, $Na_2CO_3$, $K_2CO_3$, preferably NaOH and KOH, and even more preferably NaOH. The product of step 4(a) is the free amine compound of formula XII.

Step 4(b):

The compound of formula V from step 3 is dissolved in a suitable solvent and mixed with the compound of formula XII from step 4(a). Non-limiting examples of suitable solvents include alcohol solvents (such as, for example, methanol, ethanol, isopropanol, n-propanol, n-butanol, and sec-butanol), nitrile solvents (such as, for example, acetonitrile), ether solvents (such as, for example, diethylether, THF, dibutylether, and t-butylmethylether), and toluene, more preferably alcohol solvents and nitrile solvents, and more preferably alcohol solvents. The alcohol solvent is preferably n-propanol. A catalytic amount of base is optionally added to the reaction mixture. Suitable bases include organic bases, pyridine or —$N(R^3)_3$ wherein each $R^3$ is independently selected from the group consisting of: alkyl (such as, for example, ethyl, isopropyl, propyl and butyl), aryl (such as, for example, phenyl and tolyl (e.g., p-tolyl)), and aralkyl (such as, for example, benzyl). Preferably, the base is —$N(R^3)_3$. Even more preferably, the base is diisopropylethylamine. The reaction mixture is kept at a temperature ranging preferably from about 10° C. to about 150° C., more preferably from about 40° C. to about 80° C., and even more preferably from about 60° C. to about 70° C., for about 12 hours or until the reaction is complete. The compound of formula XII can be added in any molar ratio with respect to the compound of formula V, preferably in about 1 molar equivalent with respect to the compound of formula V, more preferably in about 1.1 molar equivalents with respect to the compound of formula V. The product is the compound of formula 1, which can be crystallized upon addition of water.

The compound of formula XI is prepared following Scheme II:

Scheme II

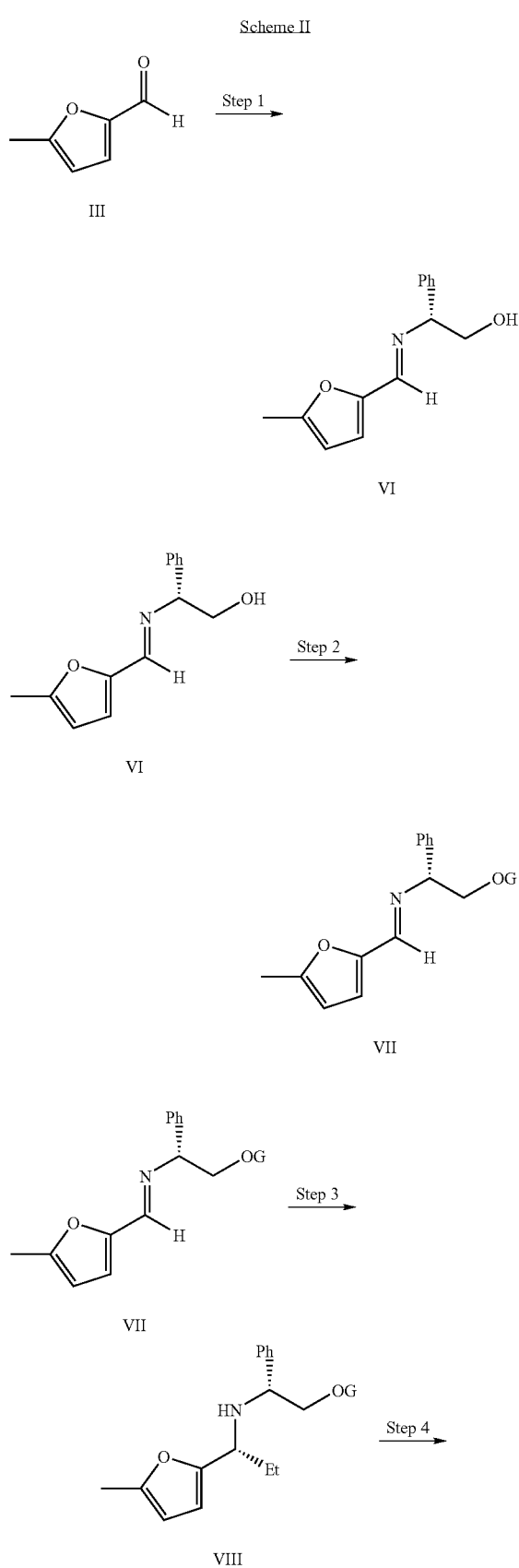

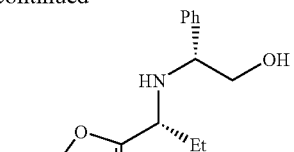

IX

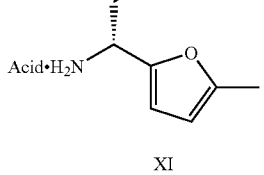

IX

Ph
‖
N
⋮
O
Et

X

Acid·H₂N

XI

Step 1:

The compound of formula III is mixed with R-2-(−)-phenylglycinol in a suitable solvent. The R-2-(−)-phenylglycinol can be used generally in at least about 0.01 molar equivalent with respect to the compound of formula III, preferably from about 0.5 to about 1.5 molar equivalents, more preferably from about 0.9 to about 1.1 molar equivalents. Non-limiting examples of suitable solvents include aromatic solvents such as benzene, toluene, and the like, halogenated solvents such as dichloromethane, methylene chloride, chlorobenzene, and the like, alcohol solvents such as methanol, ethanol, propanol, isopropanol, n-propanol, butanol, and the like, nitrile solvents such as acetonitrile, THF, and the like, ether solvents such as t-butylmethylether, THF, and the like, and mixtures thereof. Preferred solvents include benzene, toluene, THF, dichloromethane, or mixtures thereof, more preferably THF. The solution is heated at reflux for about 2 hours or until the reaction is complete. Step 1 provides the imine compound of Formula VI.

Step 2:

The solution containing the compound of Formula VI from step 1 is mixed with a silylating reagent and an acid. Suitable silylating reagents include hexamethyldisilazane, TMS chloride, TMSOTF, and the like, wherein the TMS chloride or TMSOTF is used in combination with an aryl or alkyl base. Preferred silylating agents include hexamethyldisilazane, TMS chloride, TMSOTF, wherein the TMS chloride or TMSOTF is used in combination with triethylamine. More preferably, the silylating agent is hexamethyldisilazane. Non-limiting examples of suitable acids include ammonium sulphate, ammonium nitrate, ammonium chloride, $H_2SO_4$, HCl, $H_3PO_4$, citric acid, mesyl chloride, paratoluenesulfonic acid, paratoluenesulfonic acid pyridinium salt, alkylsulfonic acid, and the like, or mixtures thereof. Preferred acids include weaker acids such as ammonium sulphate, ammonium nitrate, or ammonium chloride, more preferably ammonium sulphate. The acid can be used generally in at least about 0.2 molar equivalent with respect to the compound of formula VI, preferably at least about 0.4 molar equivalents, even more preferably at least about 0.5 molar equivalents. The mixture is heated at reflux for about 2 hours or until the reaction is complete. The mixture is preferably filtered and concentrated to provide a protected imine compound of Formula VII.

Step 3:

The imine compound of Formula VII from step 2 is added to an organometallic reagent in a suitable solvent and then worked up to provide a compound of Formula VIII. The temperature of the reaction can range from about 0° C. to about 80° C., preferably from about 10° C. to about 50° C., more preferably from about 20° C. to about 35° C. Non-limiting examples of suitable organometallic reagents include diethyl zinc, ethylzinc bromide, ethylzinc chloride, ethylmagnesium bromide, ethylmagnesium chloride or ethyllithium, preferably ethylmagnesium bromide or ethylmagnesium chloride, more preferably ethylmagnesium bromide. The organometallic reagent can be used from about 0.1 to about 5 molar equivalents with respect to the compound of formula VIII, more preferably from about 1 to about 5 molar equivalents, most preferably from about 2 to about 3 molar equivalents. Non-limiting examples of suitable solvents for the organometallic reagent include benzene, toluene, ether solvents such as TBME or THF, DME, dimethoxyethane, and the like, or mixtures thereof. Preferred solvents include ether solvents such as THF, TBME, and the like, or mixtures thereof, more preferably TBME.

Step 4:

The compound of formula VIII from step 3 was slowly added to an aqueous acid cooled to a temperature ranging from about −5° C. to about 20° C., preferably from about 0° C. to about 15° C., more preferably from about 0° C. to about 10° C. Non-limiting examples of suitable acids include $H_2SO_4$, HCl, $H_3PO_4$, citric acid, ammonium chloride, and the like, or mixtures thereof. Preferred acids include $H_2SO_4$, HCl, $H_3PO_4$, and the like, or mixtures thereof, more preferably $H_2SO_4$. The amount of acid that can be used can range from about 2.5 to about 5 molar equivalents with respect to the compound of formula VIII, preferably from about 2.5 to about 3 molar equivalents, even more preferably about 2.5 molar equivalents. Water and a co-solvent were then added to the reaction mixture. The co-solvent is preferably an alcohol. Non-limiting examples of suitable co-solvents include methanol, ethanol, propanol, isopropanol, butanol, sec-butanol, pentanol, hexanol, heptanol, octanol, and the like, or mixtures thereof. Preferred co-solvents include propanol, isopropanol, butanol, sec-butanol, pentanol, hexanol, or mixtures thereof, more preferably sec-butanol. The mixture is stirred for 0.5 hours or until any salts are dissolved. A base is then added to the mixture to adjust the pH of the aqueous phase to obtain the compound of formula IX. The pH of the aqueous phase is preferably adjusted to about 9 to about 13, more preferably to about 10 to about 11, and even more preferably to about 11. Non-limiting examples of suitable bases that can be added include an ammonium hydroxide, metal hydroxide, metal oxide, metal carbonate, metal bicarbonate, and the like, or mixtures thereof, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc cadmium, mercury and cerium. Non-limiting examples of suitable bases also include bases wherein the base is a metal salt (e.g., Li, Na, K, and Mg, and preferably Na) of a $(C_1-C_{12})$alkanol (e.g., methanol, ethanol, propanol, and isopropanol, and preferably methanol), or a $(C_3-C_{12})$cycloalkanol (e.g., cyclopentanol, cyclohexanol and cyclooctanol, and preferably cyclohexanol), and the like, or mixtures thereof. Preferred bases include a metal hydroxide, and more preferably KOH, NaOH, $NH_4OH$, LiOH and CsOH.

Step 5:

The compound of formula IX from step 4 is dissolved in a suitable solvent (such as, for example, water, methanol, ethanol, propanol, isopropanol, butanol, sec-butanol, pentanol, hexanol, tetrahydrofuran, 1,2-dimethoxyethane, 1,2-diethoxymethane, diglyme, 1,4-dioxane, or mixtures thereof, and preferably ethanol) and cooled to a temperature ranging from about −5° C. to about 20° C., preferably from about 0° C. to about 15° C., more preferably from about 0° C. to about 10° C. To this solution is added $R^4NH_2$, wherein $R^4$ is selected from the group consisting of alkyl (such as, for example, methyl, ethyl, propyl and butyl), cycloalkyl (such as, for example, cyclohexyl), heterocycloalkyl (such as, for example, piperidinyl and pyrrolidinyl), aryl (such as, for example, phenyl), heteroaryl (such as, for example, pyridyl), and aralkyl (such as, for example benzyl). Thus, examples of $R^4NH_2$ include, for example, methylamine, ethylamine, propylamine, butylamine, 1-(2-aminoethyl)piperidine, 1-(2-aminoethyl)pyrrolidine, cyclohexylamine, aniline, 2-aminopyridine, 3-aminopyridine, 4-aminopyridine, and benzylamine. Preferably, $R^4$ is $(C_1-C_6)$alkyl, more preferably $(C_1-C_3)$alkyl. The addition of $R^4NH_2$ is followed by the addition of an agent such as $NaIO_4$, $Pb(OAc)_4$, or $H_5IO_6$, and the like, or mixtures thereof. The reaction mixture is stirred for about 2 hours or until the reaction is complete to produce the compound of formula X.

Step 6:

The compound of formula X from step 5 is dissolved in 200 mL of a suitable solvent. Non-limiting examples of suitable solvents include hydrocarbon solvents such as toluene, xylene, chlorobenzene, dichlorobenzene, and the like, or ethers such as $C_4-C_{12}$ alkyl ethers (e.g., diethyl ether, dipropyl ether and dibutyl ether), 1,2-dimethoxyethane, 1,2-diethoxyethane, diglyme, 1,4-dioxane, tetrahydrofuran, and the like, or mixtures thereof. This solution is added to a solution of an acid to form a salt at a temperature ranging preferably from about −50° C. to about 80° C., more preferably from about −20° C. to about 20° C., even more preferably from about 0° C. to about 10° C. Non-limiting examples of acids include sulfonic acids, tartaric acids, $H_2SO_4$, HCl, $H_3PO_4$, HBr, carboxylic acids (e.g., acetic acid, benzoic acid and camphoric acid), and the like, and mixtures thereof. Preferred acids are sulfonic acids. Non-limiting examples of sulfonic acids include paratoluene sulfonic acid (pTSA) and alkylsulfonic acids (e.g., methane sulfonic acid and ethane sulfonic acid), with pTSA being preferred. The compound of formula XI formed is preferably crystallized from an organic solution.

For the process described in Embodiment No. 2, the compounds of formulas IV(i), XI, and XII are prepared according to the procedures in Schemes I and II. The compound of formula XII is reacted with Q to obtain the compound of formula XIII using the same reagents and reaction conditions described in Scheme I to react the compound of formula V with the compound of formula XII. Then the compound of formula IV(i) is reacted with the compound of formula XIII to obtain the compound of formula I using the same reagents and reaction conditions described in Scheme I to react the compound of formula IV(i) with the compound of formula Q.

The following nonlimiting examples are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention.

PREPARATIVE EXAMPLE 1

Preparation of Compound XI(a)

The compound of formula XI(a) was prepared following Scheme III:

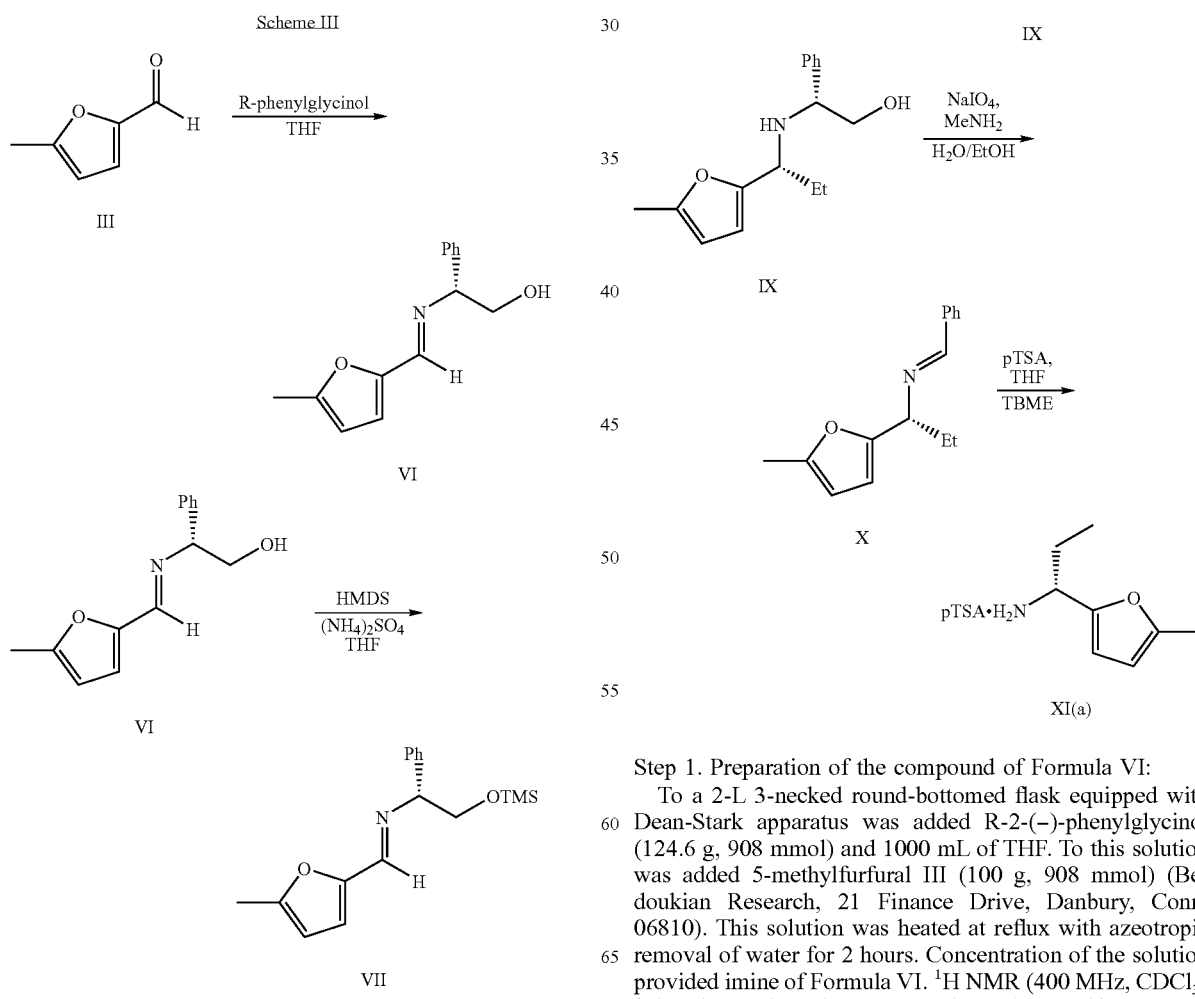

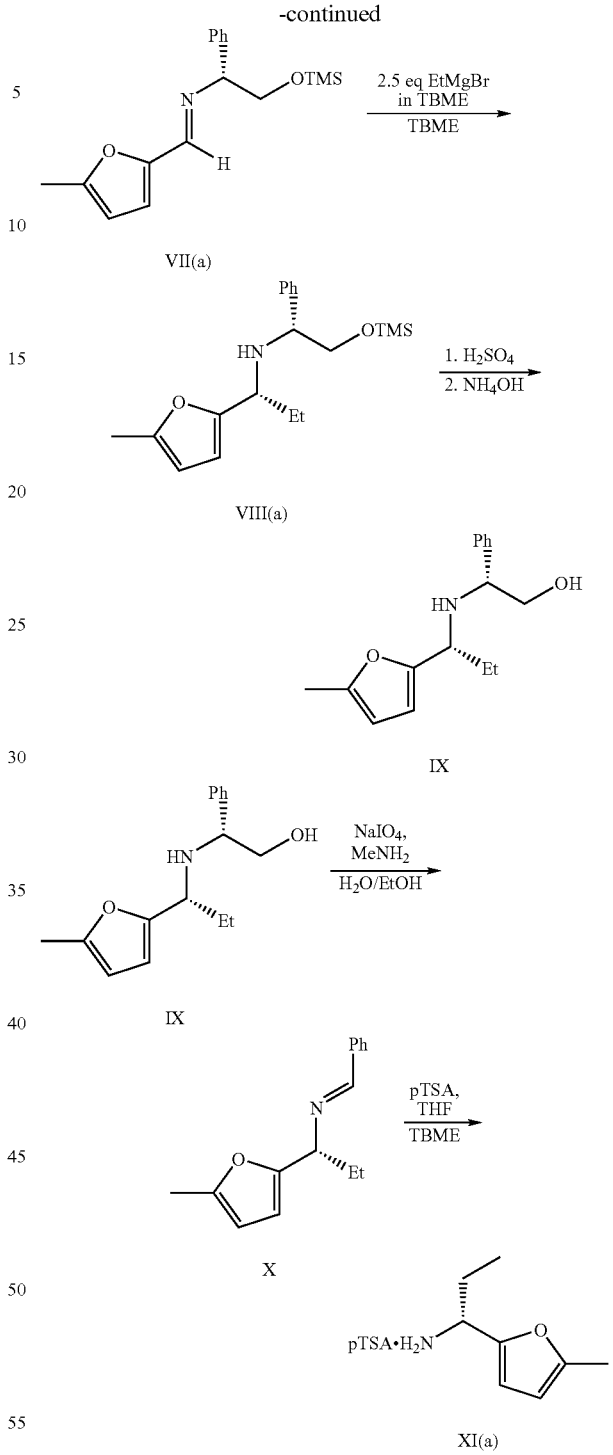

Step 1. Preparation of the compound of Formula VI:

To a 2-L 3-necked round-bottomed flask equipped with Dean-Stark apparatus was added R-2-(−)-phenylglycinol (124.6 g, 908 mmol) and 1000 mL of THF. To this solution was added 5-methylfurfural III (100 g, 908 mmol) (Bedoukian Research, 21 Finance Drive, Danbury, Conn. 06810). This solution was heated at reflux with azeotropic removal of water for 2 hours. Concentration of the solution provided imine of Formula VI. $^1$H NMR (400 MHz, CDCl$_3$) δ (ppm) 8.04 (s, 1H), 7.44–7.25 (m, 5H), 6.68 (d, J=3.3 Hz, 1H), 6.09 (dd, J=3.3, 0.8 Hz, 1H), 4.42 (dd, J=8.9, 4.2 Hz, 1H), 4.08 (dd, J=8.9, 4.2 Hz, 1H), 3.91 (dd, J=11.4, 4.2 Hz, 1H), 3.12 (br, s, 1H), 2.39 (s, 3H). $^{13}$C NMR (100.62 MHz, CDCl$_3$) δ (ppm) 156.2, 151.8, 150.2, 140.9, 128.9, 127.9, 127.8, 117.5, 108.7, 77.8, 67.9, 14.4.

Step 2. Preparation of the Compound of Formula VII(a):

The solution of Formula VI was added to ammonium sulphate (12 g, 91 mmol). Hexamethyldisalazane (73.3 g, 454 mmol) was added over 0.5 hour. The mixture was heated at reflux for 2 hours. The mixture was filtered and concentrated to an oil to provide TMS protected imine of Formula VII(a). $^1$H NMR (400 MHz, CDCl$_3$) δ (ppm) 8.01 (s, 1H), 7.43–7.18 (m, 5H), 6.60 (d, J=3.3 Hz, 1H), 6.01 (dd, J=3.3, 0.9 Hz, 1H), 4.29 (dd, J=7.3, 5.8 Hz, 1H), 3.88 (br, unresolved d, 1H), 3.86 (d, J=2.4 Hz, 2H), 2.32 (s, 3H), 0 (s, 9H). $^{13}$C NMR (100.62 MHz, CDCl$_3$) δ (ppm) 155.9, 151.7, 150.6, 141, 128.7, 127.9, 127.6, 116.9, 108.5, 77.3, 68.0, 14.4, 2.4, 0.

Step 3. Preparation of the Compound of Formula VIII(a):

To a 5 L 3-necked round bottomed flask containing EtMgBr 1 M in TBME (2270.5 mL, 2.27 mol) at 20° C. was added imine of Formula VII(a) while maintaining the temperature below 35° C. After addition was completed, an aliquot was removed and quenched into a saturated solution of ammonium chloride, extracted with TBME, and concentrated to an oil to provide an imine of Formula VIII(a). $^1$H NMR (400 MHz, CDCl$_3$) δ (ppm) 7.23–7.09 (m, 5H), 5.81 (d, J=3 Hz, 1H), 5.67 (dd, J=3, 1 Hz, 1H), 3.77 (dd, J=8.1, 4.6 Hz, 1H), 3.56 (dd, J=10.1, 4.6 Hz, 1H), 3.5 (br, unresolved dd, 2H), 2.11 (s, 3H), 1.73–1.62 (m, 2H), 0.74 (t, J=7.4 Hz, 3H), 0 (s, 9H).

Step 4. Preparation of the Compound of Formula IX:

A solution of the amine compound of Formula VIII(a) was slowly added over 1 hour to 1000 mL of 2.5M sulfuric acid cooled to 10° C. After addition was completed, 500 mL of sec-butanol and 500 mL of water was added and the mixture was stirred for 0.5 hours to dissolve any salts formed. The mixture was then transferred to a separatory funnel and the bottom aqueous layer separated. To the top organic phase was added 250 mL of 25% ammonium hydroxide until the pH of the aqueous phase was 11. The bottom aqueous phase was separated and the organic phase washed twice with 500 mL of 5% brine solution. The organic phase was then treated with 20 g of Darco and 20 g of celite and filtered. The organic phase was concentrated to an oil to provide an amine compound of Formula IX. $^1$H NMR (400 MHz, CDCl$_3$) δ (ppm) 7.22–7.12 (m, 5H), 5.84 (d, J=2.99 Hz, 1H), 5.69 (dd, J=2.99, 1 Hz, 1H), 3.72 (dd, J=7.3, 4.6 Hz, 1H), 3.62 (dd, J=10.8, 4.6 Hz, 1H), 3.49–3.43 (m, 2H), 2.07 (s, 3H), 1.73–1.62 (m, 2H), 0.77 (t, J=7.4 Hz, 3H). $^{13}$C NMR (100.62 MHz, CDCl$_3$) δ (ppm) 154.9, 151.4, 141.8, 128.9, 127.8, 127.7, 107.8, 106.1, 66.4, 62.3, 56.4, 27.6, 14, 11.1.

Step 5. Preparation of the Compound of Formula X:

The amine of Formula IX was dissolved in 500 mL EtOH and cooled to 0° C. To this solution was added MeNH$_2$ (40% by wt. In H$_2$O) (80 mL, 928 mmol) followed by addition of a solution of NaIO$_4$ (200 g, 934 mmol) dissolved in 1000 mL H$_2$O. After stirring 2 hours at room temperature, the reaction is filtered and the inorganic solids rinsed with 600 mL methy t-butyl ether (TBME). The filtrate was separated and the organic phase washed with 1000 mL H$_2$O and then with 1000 mL of 5% NaCl solution. After concentration of the organic phase an oil was obtained of intermediate of Formula X. The oil is dissolved in 200 mL THF. $^1$H NMR (400 MHz, CDCl$_3$) δ (ppm) 8.17 (s, 1H), 7.64–7.62 (m, 2H), 7.27–7.24 (m, 3H), 5.96 (d, J=3 Hz, 1H), 5.75 (dd, J=3, 0.9 Hz, 1H), 4.09 (dd, J=8.1, 5.8 Hz, 1H), 2.11 (s, 3H), 1.97–1.78 (m, 2H), 0.79 (t, J=7.4 Hz, 3H).

Step 6. Preparation of the Compound of Formula XI(a):

The solution containing the compound of formula X from step 5 was added to a solution of p-toluene sulfonic acid (160 g, 840 mmol) dissolved in 400 mL THF at 0° C. This solution was stirred at 25° C. for 1–4 hours and then diluted with 600 mL TBME. After stirring at 25° C. for 6–14 hours, the heterogeneous reaction mixture was filtered and the solids were washed with 800 mL 3:1 TBME/THF and dried in a vacuum oven at 40° C. for 6 hrs to provide the compound of formula XI(a) 75–80% yield. The compound of formula. XI(a) was used to prepare the compound of formula I as described earlier. $^1$H NMR (400 MHz, CDCl$_3$) δ (ppm) 8.09 (br s, 3H), 7.68 (d, J=7.4 Hz, 2H), 7.15 (d, J=7.6 Hz, 2H), 6.22 (d, J=3.2 Hz, 1H), 5.82 (dd, J=3.1, 1 Hz, 1H), 4.05 (dd, J=8, 6.5 Hz, 1H), 2.38 (s, 3H), 2.14 (s, 3H), 1.9–1.83 (m, 2H), 0.74 (t, J=7.4 Hz, 3H). $^{13}$C NMR (100.62 MHz, DMSO-d$_6$) δ 152.2, 148.3, 145.6, 137.8, 128.1, 125.5, 110.2, 106.8, 47.9, 24.9, 20.8, 13.3, 9.9. Mp 117° C. HRMS calcd for C$_8$H$_{14}$NO (FAB+ m/z M+H) 140.1075, found 140.1072. Anal. calcd. for C$_{15}$H$_{21}$NO$_4$S: C, 57.86; H, 6.80; N, 4.50. Found: C, 57.90; H, 6.93; N, 4.26.

PREPARATIVE EXAMPLE 2

Preparation of Compound XIII(a)

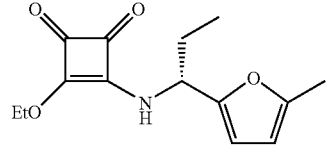

XIII(a)

To a mixture containing 3,4-diethoyl-3-cyclobutene-1,2-dione (diethyl squarate, 2.53 g, 14.88 mmol, 1.05 eq), and compound XI(a) (4.41 g, 14.16 mmol, 1.0 eq) in ethanol (27 ml) was charged triethyalmine (2 ml, 14.23 mmol, 1.0 eq). The batch was stirred at ambient temperature for 3 hours, filtered through a silica gel pad, washed with ethanol and concentrated. The resulting oil was purified via column chromatography to afford compound XIII(a), thick colorless oil, in 97.2% yield (3.625 g). $^1$HNMR (400 MHz, DMSO-d$_6$) δ (ppm) 9.16 (br d, 0.5H), 8.97 br d, 0.5H), 6.17 (s, 1H), 6.01 (s, 1H), 5.02 (br m, 0.5H), 4.67 (m, 2H), 4.54 (br m, 0.5H), 2.22 (s, 3H), 1.92 (m, 0.5H), 1.82 (m, 0.5H), 1.37 (t, J=7.0 Hz, 3H), 0.90 (t, J=7.3 Hz, 3H). $^{13}$CNMR (DMSO-d$_6$) δ (ppm) 189.14, 188.94; 182.41, 182.09; 177.11, 176.62; 172.42, 171.76; 152.45, 152.01; 151.15, 107.34; 106.38; 68.91; 53.92, 52.99; 26.08, 25.90; 15.59; 13.22; 10.44. FAB+m/z 264.2 (M+H).

EXAMPLE 1

The compound of formula I was prepared following Scheme IV:

Scheme IV

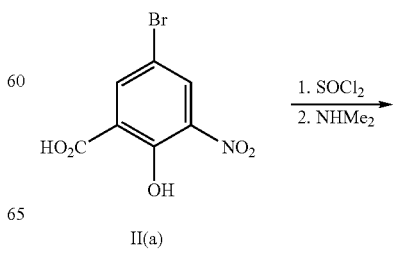

II(a)

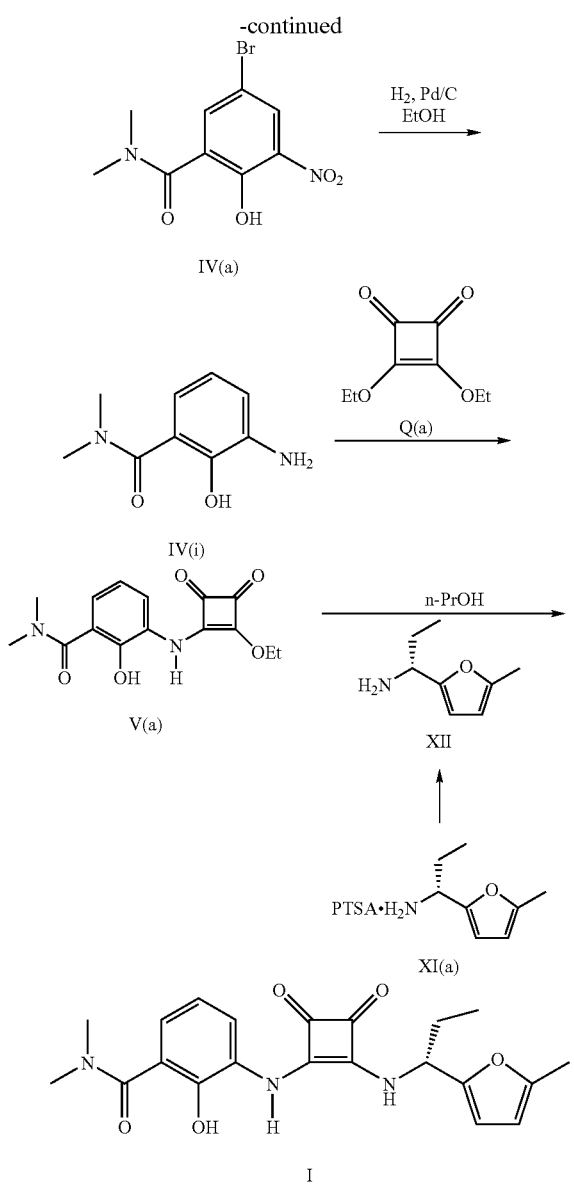

Step 1: Preparation of 2-Hydroxy-N,N-diemethylbenzamide (IVa)

To a three neck flask was charged (50.0 g, 190.8 mmol) of 5-bromo-3-nitrosalicylic acid (Davos, 464 Hudson Terrace, Englewood, N.J. 07362), 200 ml of acetonitrile and 14 ml (191.9 mmol) of thionyl chloride. The resulting mixture was heated at 70° C. for 2 hours. The mixture was then cooled to 5–10° C. and a solution of dimethylamine in THF (2M, 210 ml, 2.2 eq.) was added slowly over one hour. The reaction mixture was then warmed to ambient temperature and stirred for another 3 hours. The mixture was mixed with 100 ml of water and acidified with sulfuric acid (2N, 45 ml) to a pH of 2. Additional 800 ml of water was added slowly over one hour while solids product precipitated out from the mixture. The suspension was cooled to 5° C. The solids were filtered and washed with water (200 ml). The wet crude product was recrystallized from 400 ml of hot ethanol to give 44.2 g (80%) of the compound of formula IV(a).

Melting point: 181° C.–183° C. $^1$H NMR (400 MHz, DMSO): δ (ppm) 10.94 (s, 1H), 8.16 (d, 1H, J=2.5 Hz), 7.76 (d, 1H, J=2.5 Hz), 2.9 (br, 6H). $^{13}$C NMR (100.62 MHz, DMSO): 164.7, 147.5, 137.6, 135.9, 131.5, 127.4, 110.0, 37.6, 34.3. Anal. calcd. for $C_9H_9BrN_2O_4$ (289.08): C, 37.39; H, 3.14; N, 9.69. Found: C, 37.42; H, 2.90; N, 9.55.

Step 2: Preparation of 5-bromo-2-hydroxy-3-nitro-N,N-dimethylbenzamide (Va)

A mixture of 25.0 g (86.5 mmol) of compound IV(a), 5.5 g of 5% Pd/C (50% water), 12.3 g (88.8 mmol) of potassium carbonate and 200 ml of ethanol was pressurized under hydrogen at 105 psi with agitation at room temperature for 10 hours. The reaction mixture was analyzed by $^1$H NMR (400 MHz, CDCN): δ (ppm) 2.9 (s, 6H), 3.9 (br, 2H), 6.47 (q, 1H), 6.55 (m, 2H). If the conversion of compound IV(a) to intermediate IV(i) was found not complete, additional 0.5 g of Pd/C catalyst was charged and the mixture was kept under hydrogen pressure at 105 psi for 5 more hours. The mixture was then filtered through a Celite bed and the cake was washed with 30 ml of ethanol. Caution should be taken to ensure minimum exposure of the product solution to air during the filtration. The filtrate was immediately transferred into one-liter three neck flask fitted with a reflux condenser, mechanic stirrer, and nitrogen inlet. The solution was cooled to 5° C. and a solution of 19.9 g (116.7 mmol, 1.35 eq.) of 3,4-diethoxy-3-cyclobutene-1,2-dione (diethyl squarate) (Compound of formula Q(a)) (Lonza, Inc. Corporate Headquaters, 17–17 Route 208, Fair Lawn, N.J. 07410) in 80 ml ethanol was added in one portion. The solution was slowly warmed up to 25° C. in 2 hours. If there were no product solids precipitating from the reaction mixture, a small amount (~100 mg) of potassium carbonate was added. The suspension was stirred for another 5 hours at room temperature. The mixture was then slowly heated to reflux over 1 hour before it was slowly cooled to 10° C. over 2 hours. During the heating, a small amount of compound IV(i) trapped inside the product solids was released and converted to the product V(a). The solids were collected by filtration and the cake was washed with 40 ml of cool ethanol. The solids were dried in a vacuum oven at 60° C. for 5 hours to give 21.3 g (80.9%) of the compound of formula V(a). $^1$H NMR (400 MHz, CD$_3$CN): δ (ppm) 1.4 (t, 3H), 3.1 (s, 6H), 4.8 (q,2H), 6.9 (dd,3H), 7.2 (d,1H), 7.6 (d,1H), 8.1 (br, 1H), 10.5 (br,1H). Mp: 180–183° C. $^{13}$C NMR (100.62 MHz, DMSO): 188.2, 184.1, 178.0, 171.3, 167.9, 146.9, 125.9, 125.8, 125.7, 125.6, 119.3, 68.1, 37.6, 34.6, 15.6. Anal. calcd. for $C_{15}H_{16}N_2O_5$ (304.30): C, 59.21; H, 5.30; N, 9.21. Found: C, 59.12; H, 5.29; N, 9.14.

Step 3: Preparation of 2-Hydroxy-N,N-dimethyl-3-[[2-[[1(R)-(5-methyl-2-furanyl)propyl]amino]-3,4-dioxo-1-cyclobuten-1-yl]amino]benzamide (Compound I)

Method A:

A mixture containing 10.0 g (32.9 mmol) of compound V(a), 11.1 g (35.6 mmol, 1.08 eq.) of compound XI(a) from Scheme III, 6.2 ml (44.4 mmol, 1.35 eq.) of triethylamine and 120 ml of acetonitrile was heated at 65° C. with agitation for 4 hours. The mixture was then cooled to 50° C. and 2.0 g of charcoal was added. The resulting suspension was heated at 70° C. for 1 hour. The reaction mixture was cooled to 40° C. and filtered through a Celite bed. The Celite cake was washed with 30 ml of acetonitrile. The filtrate was charged back to a three neck flask and about 12 ml of 1N sulfuric acid was added slowly until the pH of the mixture was about 4. Water (180 ml) was added slowly at 50° C. over one hour and the resulting suspension was cooled to 15° C. over 1 hour. The solids were collected by filtration and the cake was washed with 50 ml of water. The $^1$H NMR of the wet cake showed that the product was contaminated by about 15% p-toluenesulfonic acid. The wet cake was charged back to a three neck flask along with 130 ml of acetonitrile. The mixture was heated to 70° C. to dissolve all solids. Water (150 ml) was added slowly over half an hour at 55° C. with good agitation. The resulting suspension was cooled to 10° C. over one hour. The solids were collected by filtration and the cake was washed with 40 ml of water. The product was dried in a vacuum oven over night at 60° C., to give 10.6 g (77.6%) of the title compound I, Mp: 83° C. $^1$H NMR (400 MHz, DMSO): δ (ppm) 1.0 (t,3H), 1.9 (m, 1H), 2.0 (m,1H), 2.3 (s,3H), 3.0 (S, 6H), 5.2 (dd,1H), 6.1 (d,1H), 6.3 (d, 1H), 6.9 (m, 2H), 7.8 (d, 1H), 8.7 (d, 1H), 9.3 (dr,1H), 10.0 (br, 1H). $^{13}$CNMR (100.62, CD$_3$CN): 185.2, 182.0, 171.8, 170.1, 164.6, 153.4, 153.0, 148.9, 129.2, 124.1, 122.9, 119.4, 119.0, 108.4, 107.2, 54.8, 38.7, 28.3, 13.5, 10.6.

Method B:

To a three neck round bottom flask were charged 41.2 g (132.4 mmol) of compound XI(a), 200 ml of water and 100 ml of t-butyl methylether. The solution was agitated and a 25% sodium hydroxide solution (18 ml) was added slowly over 20 min while maintaining the temperature of the reaction mixture below 30° C. The resulting solution was transferred into a separation funnel and the aqueous was extracted another two times with 100 ml of t-butyl methylether. The combined organic was washed with 100 ml of saturated sodium chloride solution. The solvent was removed under vacuum and the residue containing free amine XII was dissolved in 360 ml of n-propanol. The resulting solution was mixed with 40.0 g (128.5 mmol) of compound V(a) and 0.4 g (3.1 mmol, 0.024 eq.) of diisopropylethylamine. The mixture was heated at 65° C. for 12 hours. Another 120 ml of n-propanol and 400 ml of water was charged. The mixture was then heated up to about 70° C. and slowly cooled to 10° C. The solids were collected by filtration and washed with 80 ml of aqueous solution containing 50% of n-propanol. The resulting wet cake was dried in a vacuum oven at 60° C. over night, to give 44.7 g (81.9%) of the compound of formula I.

For the process described in Embodiment No. 2, the compounds of formulas IV(i), XI(a), and XII are prepared according to the procedures in Schemes III and IV.

The compound of formula XII is reacted with Q to obtain the compound of formula XIII using the same reagents and reaction conditions described in Scheme I to react the compound of formula V with the compound of formula XII. Then the compound of formula IV(i) is reacted with the compound of formula XIII to obtain the compound of formula I using the same reagents and reaction conditions described in Scheme I to react the compound of formula IV(i) with the compound of formula Q.

EXAMPLE 2

To a solution of 0.58 g (2.20 mmol) of compound XIII(a) in 25 ml ethanol were added 20 mg potassium carbonate (~0.02 eq.) and a solution of 3 mmol of active compound of formula IV(i) (1.36 eq) in 10 ml of ethanol. The resulting mixture was heated at 60° C. for about 3.5 hours. Upon completion of the reaction, compound I was isolated via the same procedure as the method B, in similar yield (83% by assay).

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

What is claimed is:

1. A process for preparing a compound of formula I:

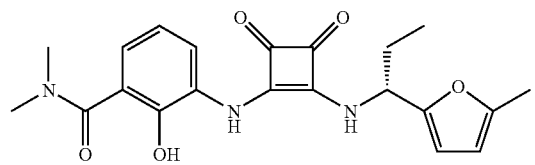

comprising:

(a) converting the compound of formula II

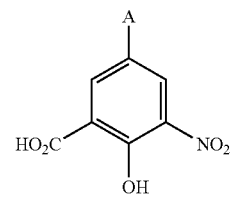

to a compound of formula IV:

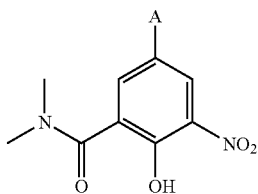

wherein A, in compounds of formulas II and IV, is selected from the group consisting of Br, Cl and I;

(b) hydrogenating the compound of formula IV with a suitable hydrogenation catalyst under hydrogen pressure, to form the intermediate compound of formula IV(i):

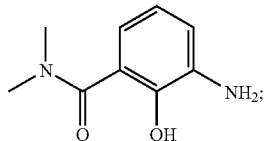

IV(i)

(c) reacting the compound of formula IV(i) with a compound of formula Q:

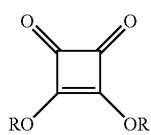

Q wherein R represents $(C_1–C_{10})$alkyl, to yield a compound of formula V:

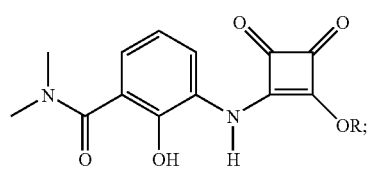

V (d) converting the compound of formula III

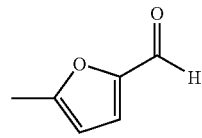

III to a compound of formula VI:

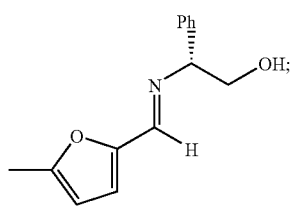

VI (e) adding a protecting group to the compound of formula VI to yield a compound of formula VII:

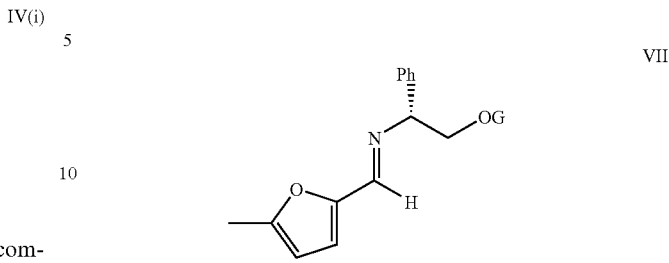

VII wherein G represents a protecting group;

(f) reacting the compound of formula VII with a suitable organometallic reagent, followed by work-up, to yield a compound of formula VIII:

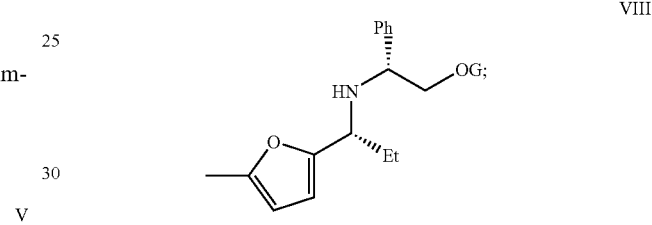

VIII (g) removing the protecting group (G) from the compound of formula VIII to yield a compound of formula IX:

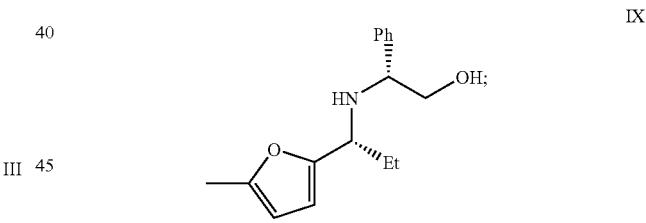

IX (h) converting the compound of formula IX into an imine intermediate compound of formula X:

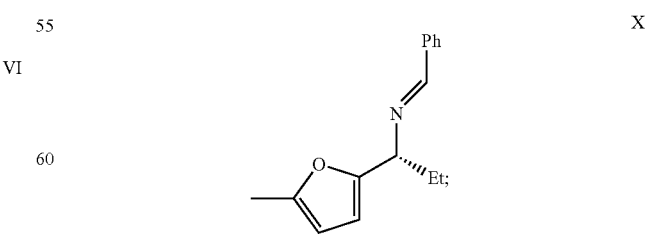

X (i) converting the imine intermediate compound of formula X into the salt of formula XI:

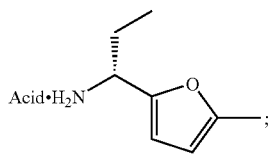

(j) reacting the compound of formula XI with the compound of formula V to yield the compound of formula I; or (k) converting the compound of formula XI to the free amine:

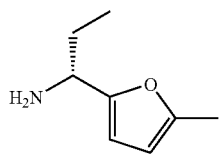

and reacting the compound of formula XII with the compound of formula V to yield the compound of formula I.

2. The process of claim 1 wherein said compound of formula XI in step (i) is converted to the compound of formula XII:

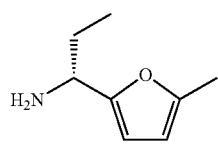

by reacting said compound of formula XI in a suitable solvent with a suitable base, and then the compound of formula XII is reacted with the compound of formula V to produce the compound of formula I.

3. The process of claim 1 wherein substituent A is Br.

4. The process of claim 1 wherein G represents a protecting group selected from the group consisting of: silylating reagents and esters.

5. The process of claim 1 wherein the acid in said compound of formula XI is selected from the group consisting of: sulfonic acids, tartaric acids, $H_2SO_4$, HCl, $H_3PO_4$, HBr, and carboxylic acids, and mixtures thereof.

6. The process of claim 1 wherein step (a) comprises reacting said compound of formula II with a suitable acid chloride in a suitable solvent at a suitable temperature, and then reacting the resulting reaction mixture with dimethylamine.

7. The process of claim 1, wherein step (b) comprises making a mixture of said compound of formula IV, a hydrogenation catalyst, and a suitable base, and pressurizing the mixture under $H_2$ pressure.

8. The process of claim 1 wherein step (c) comprises adding 3,4-dialkoxy-3-cyclobutene-1,2-dione to said compound of formula IV(i) from step (b), adjusting the temperature to about 0° C. to about 80° C. to yield a compound of formula V.

9. The process of claim 1 wherein step (d) comprises mixing a solution of R-2-(−)-phenylglycinol with said compound of formula III, and heating the resulting solution at reflux with azeotropic removal of water to provide the imine compound of Formula VI.

10. The process of claim 1 wherein step (e) comprises mixing an acid and a silylating reagent with the compound of formula VI from step (d), and heating the solution at reflux to provide a protected imine compound of formula VII.

11. The process of claim 1 wherein the organometallic reagent, in step (f), is in a suitable solvent, and said organometallic reagent is selected from the group consisting of: diethyl zinc, ethylzinc bromide, ethylzinc chloride, ethylmagnesium bromide, ethylmagnesium chloride and ethyllithium.

12. The process of claim 1 wherein step (g) comprises deprotecting the imine compound of formula VIII from step (f) with an acid, followed by treatment with a base to form said compound of formula IX.

13. The process of claim 1 wherein step (h) comprises dissolving the compound of formula IX in a suitable solvent, adding $R^4NH_2$, and, following the addition of said $R^4NH_2$, adding an additional agent selected from the group consisting of: $NaIO_4$, $Pb(OAc)_4$, $H_5IO_6$, and mixtures thereof, wherein $R^4$ is selected from the group consisting of alkyl, cycloalkyl, heterocycloalkyl, aryl, heteroaryl, and aralkyl, to provide the intermediate compound of formula X.

14. The process of claim 1 wherein step (i) comprises (1) dissolving said intermediate compound of formula X from step (h) in a suitable solvent, and (2) adding a suitable acid to provide a compound of formula XI.

15. The process of claim 1 wherein step (j) comprises combining the compound of formula XI from step (i), the compound of formula V from step (c), a suitable base and a suitable solvent, and heating the resulting reaction mixture to produce the compound of formula I.

16. The process of claim 1 wherein in step (k) a catalytic amount of base is used in the reaction of the compound of formula V with the compound of formula XII.

17. The process of claim 1 wherein:
(1) Substituent A is Br;
(2) G represents a protecting group selected from the group consisting of: silylating reagents and esters;
(3) Step (a) comprises reacting said compound of formula II with a suitable acid chloride in a suitable solvent at a suitable temperature, and then reacting the resulting reaction mixture with dimethylamine;
(4) Step (b) comprises making a mixture of said compound of formula IV, a hydrogenation catalyst, and a suitable base, and pressurizing the mixture under $H_2$ pressure;
(5) Step (c) comprises adding 3,4-dialkoxy-3-cyclobutene-1,2-dione to said compound of formula IV(i) from step (b), adjusting the temperature to about 0° C. to about 80° C. to yield a compound of formula V;
(6) Step (d) comprises mixing a solution of R-2-(−)-phenylglycinol with said compound of formula II, and heating the resulting solution at reflux with azeotropic removal of water to provide the imine compound of Formula VI;
(7) Step (e) comprises mixing an acid and a silylating reagent with the compound of formula VI from step (d), and heating the solution at reflux to provide a protected imine compound of formula VII;
(8) The organometallic reagent, in step (f), is in a suitable solvent, and said organometallic reagent is selected from the group consisting of: diethyl zinc, ethylzinc bromide, ethylzinc chloride, ethylmagnesium bromide, ethylmagnesium chloride and ethyllithium;
(9) Step (g) comprises deprotecting the imine compound of formula VIII from step (f) with an acid, followed by treatment with a base to form said compound of formula IX;
(10) Step (h) comprises dissolving the compound of formula IX in a suitable solvent, adding $R^4NH_2$, and, following the addition of said $R^4NH_2$, adding an additional agent selected from the group consisting of: $NaIO_4$, $Pb(OAc)_4$, $H_5IO_6$, and mixtures thereof, wherein $R^4$ is selected from the group consisting of alkyl, cycloalkyl, heterocycloalkyl, aryl, heteroaryl, and aralkyl, to provide the intermediate compound of formula X;
(11) Step (i) comprises (1) dissolving said intermediate compound of formula X from step (h) in a suitable solvent, and (2) adding a suitable acid to provide a compound of formula XI;
(12) Step (j) comprises combining the compound of formula XI from step (i), the compound of formula V from step (c), a suitable base and a suitable solvent, and heating the resulting reaction mixture to produce the compound of formula I; and
(13) Step (k) comprises using a catalytic amount of base in the reaction of the compound of formula V with the compound of formula XII.

18. The process of claim 17 wherein:
(1) said solvent used with said acid chloride in step (a) is selected from the group consisting of: acetonitrile, THF, t-butylmethylether, methylenechloride, toluene, ethylacetate, diethylether, and chloroform;
(2) said acid chloride in step (a) is selected from the group consisting of: thionyl chloride and oxalyl chloride;
(3) said dimethylamine in step (a) is a solution of dimethylamine wherein the solvent used in said dimethylamine solution is selected from the group consisting of: acetonitrile, THF, t-butylmethylether, methylenechloride, toluene, ethylacetate, diethylether, and chloroform;
(4) said suitable base in step (b) is selected from the group consisting of: KOH, NaOH, $Na_2CO_3$, $K_2CO_3$, $NaHCO_3$, $KHCO_3$, tetramethylguanidine, DBU, diisopropylethylamine and mixtures thereof;
(5) said hydrogenation catalyst in step (b) is selected from the group consisting of: Pd/C, Pt/C, PdOH, and raney nickel;
(6) said 3,4-dialkoxy-3-cyclobutene-1,2-dione in step (c) is 3,4-diethoxy-3-cyclobutene-1,2-dione;
(7) said acid in step (e) is selected from the group consisting of: ammonium sulphate, ammonium nitrate, ammonium chloride, $H_2SO_4$, HCl, $H_3PO_4$, citric acid, mesylchloride, paratoluenesulfonic acid, paratoluenesulfonic acid pyridium salt, alkylsulfonic acid, and mixtures thereof;
(8) said silylating reagent in step (e) is selected from the group consisting of: hexamethyldisilazane, TMS chloride, and TMSOTF, wherein said TMS chloride is used in combination with triethylamine, and said TMSOTF is used in combination with triethylamine;
(9) said suitable solvent in step (f) is selected from the group consisting of: benzene, toluene, TBME, THF, DME, dimethoxyethane, and mixtures thereof;
(10) said acid in step (g) is selected from the group consisting of: $H_2SO_4$, HCl, $H_3PO_4$, citric acid, ammonium chloride, and mixtures thereof;
(11) said base in step (g) is selected from the group consisting of: ammonium hydroxide, metal hydroxide, metal oxide, metal carbonate, metal bicarbonate, and mixtures thereof, wherein said metal is selected from the group consisting of: lithium, sodium, potassium, rubidium, cesium, beryllium, magnesium, calcium, strontium, barium, aluminum, indium, thallium, titanium, zirconium, cobalt, copper, silver, zinc cadmium, mercury and cerium;
(12) said acid in step (i) is selected from the group consisting of: sulfonic acids, tartaric acids, $H_2SO_4$, HCl, $H_3PO_4$, HBr, and carboxylic acids and mixtures thereof; and
(14) said base in step (k) is selected from the group consisting of: pyridine and $N(R^3)_3$, wherein each $R^3$ is independently selected from the group consisting of: alkyl, aryl and arylalkyl.

19. The Process of claim 18 wherein said acid in step (i) is a sulfonic acid selected from the group consisting of: paratoluene sulfonic acid and alkylsulfonic acid.

20. The process of claim 19 wherein said acid is paratoluene sulfonic acid.

21. The process of claim 18 wherein:
(1) said acid chloride in step (a) is thionyl chloride;
(2) said solvent used with said acid chloride in step (a) is acetonitrile;
(3) said hydrogenation catalyst in step (b) is Pd/C;
(4) said acid in step (i) is paratoluene sulfonic acid; and
(5) said base in step (k) is diisopropylethylamine.

22. The process of claim 18 wherein step (c) further comprises adding a base to the compound of formula IV(i), wherein said base is selected from the group consisting of: KOH, NaOH, $Na_2CO_3$, $K_2CO_3$, $NaHCO_3$, $KHCO_3$, tetramethylguanidine, DBU, diisopropylethylamine and mixtures thereof.

23. The process of claim 20 wherein step (c) further comprises adding a base to the compound of formula IV(i), wherein said base is selected from the group consisting of: KOH, NaOH, $Na_2CO_3$, $K_2CO_3$, $NaHCO_3$, $KHCO_3$, tetramethylguanidine, DBU, diisopropylethylamine and mixtures thereof.

24. The process of claim 21 wherein step (c) further comprises adding a base to the compound of formula IV(i), wherein said base is selected from the group consisting of: KOH, NaOH, $Na_2CO_3$, $K_2CO_3$, $NaHCO_3$, $KHCO_3$, tetramethylguanidine, DBU, diisopropylethylamine and mixtures thereof.

25. The process of claim 18 wherein:
(1) said dimethlyamine in step (a) is at a concentration of at least 1 molar equivalent with respect to said compound of formula II;
(2) said $H_2$ pressure in step (b) is from about 10 to about 500 psi;
(3) said 3,4-diethalkoxy-3-cyclobutene-1,2-dione in step (c) is at least 1 molar equivalent with respect to the compound of formula IV(i);
(4) said R-2-(−)-phenylglycinol in step (d) is at least about 0.01 molar equivalent with respect to said compound of formula III;
(5) said acid in step (e) is at least about 0.2 molar equivalent with respect to the compound of formula VI; and
(6) said organometallic reagent in step (f) is from about 0.1 to about 5 molar equivalents with respect to said compound of formula VII.

26. The process of claim 21 wherein:
(1) said dimethlyamine in step (a) is at a concentration of at least 1 molar equivalent with respect to said compound of formula II;
(2) said H₂ pressure in step (b) is from about 10 to about 500 psi;
(3) said 3,4-diethalkoxy-3-cyclobutene-1,2-dione in step (c) is at least 1 molar equivalent with respect to the compound of formula IV(i);
(4) said R-2-(−)-phenylglycinol in step (d) is at least about 0.01 molar equivalent with respect to said compound of formula III;
(5) said acid in step (e) is at least about 0.2 molar equivalent with respect to the compound of formula VI; and
(6) said organometallic reagent in step (f) is from about 0.1 to about 5 molar equivalents with respect to said compound of formula VII.

27. The process of claim 22 wherein:
(1) said dimethlyamine in step (a) is at a concentration of at least 1 molar equivalent with respect to said compound of formula II;
(2) said H₂ pressure in step (b) is from about 10 to about 500 psi;
(3) said 3,4-diethalkoxy-3-cyclobutene-1,2-dione in step (c) is at least 1 molar equivalent with respect to the compound of formula IV(i);
(4) said R-2-(−)-phenylglycinol in step (d) is at least about 0.01 molar equivalent with respect to said compound of formula III;
(5) said acid in step (e) is at least about 0.2 molar equivalent with respect to the compound of formula VI; and
(6) said organometallic reagent in step (f) is from about 0.1 to about 5 molar equivalents with respect to said compound of formula VII.

28. The process of claim 21 wherein the compound of formula I is produced in step (k) by reacting the compound of formula XII with the compound of formula V.

29. The process of claim 25 wherein the compound of formula I is produced in step (k) by reacting the compound of formula XII with the compound of formula V.

30. The process of claim 26 wherein the compound of formula I is produced in step (k) by reacting the compound of formula XII with the compound of formula V.

31. The process of claim 27 wherein the compound of formula I is produced in step (k) by reacting the compound of formula XII with the compound of formula V.

32. A process for making a compound of formula XI or XII:

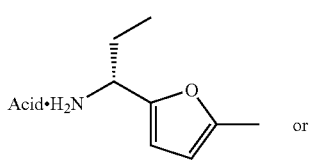

XI or

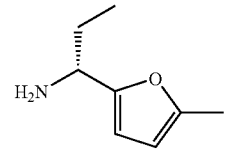

XII comprising:
(a) converting the compound of formula III

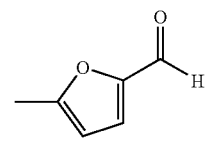

III to a compound of formula VI:

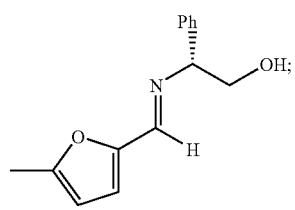

VI (b) mixing a protecting group with the compound of formula VI to yield a compound of formula VII:

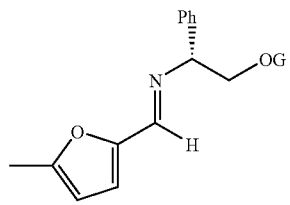

VII wherein G represents a protecting group;
(c) reacting the compound of formula VII with a suitable organometallic reagent, followed by work-up, to yield a compound of formula VIII:

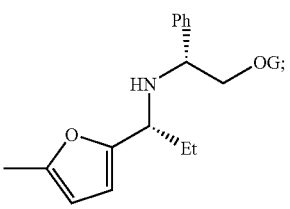

VIII (d) removing the protecting group (G) from the compound of formula VIII to yield a compound of formula IX:

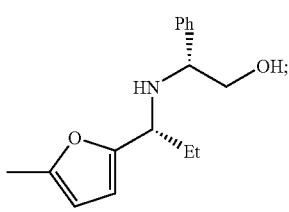

(e) converting the compound of formula IX into an imine intermediate compound of formula X:

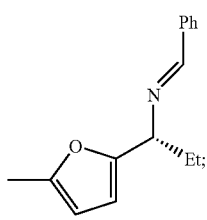

(f) converting the imine intermediate compound of formula X into the salt of formula XI:

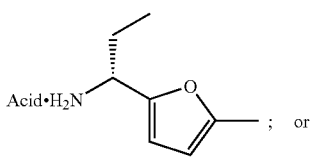

or (g) converting the compound of formula XI to the free amine:

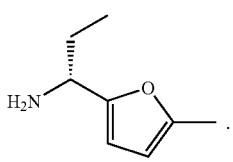

33. The process of claim 32 wherein G represents a protecting group selected from the group consisting of: silylating reagents and esters.

34. The process of claim 32 wherein the acid in said compound of formula XI is selected from the group consisting of: sulfonic acids, tartaric acids, $H_2SO_4$, HCl, $H_3PO_4$, HBr, and carboxylic acids, and mixtures thereof.

35. The process of claim 32 wherein step (a) comprises mixing a solution of R-2-(−)-phenylglycinol with said compound of formula III, and heating the resulting solution at reflux with azeotropic removal of water to provide the imine compound of Formula VI.

36. The process of claim 32 wherein step (b) comprises mixing an acid and a silylating reagent with the compound of formula VI from step (a), and heating the solution at reflux to provide a protected imine compound of formula VII.

37. The process of claim 32 wherein the organometallic reagent, in step (c), is in a suitable solvent, and said organometallic reagent is selected from the group consisting of: diethyl zinc, ethylzinc bromide, ethylzinc chloride, ethylmagnesium bromide, ethylmagnesium chloride and ethylithium.

38. The process of claim 32 wherein step (d) comprises deprotecting the imine compound of formula VIII from step (c) with an acid, followed by treatment with a base to form said compound of formula IX.

39. The process of claim 32 wherein step (e) comprises dissolving the compound of formula IX in a suitable solvent, adding $R^4NH_2$, and, following the addition of said $R^4NH_2$, adding an additional agent selected from the group consisting of: $NaIO_4$, $Pb(OAc)_4$, $H_5IO_6$, and mixtures thereof, wherein $R^4$ is selected from the group consisting of alkyl, cycloalkyl, heterocycloalkyl, aryl, heteroaryl, and aralkyl, to provide the intermediate compound of formula X.

40. The process of claim 32 wherein step (f) comprises (1) dissolving said intermediate compound of formula X from step (e) in a suitable solvent, and (2) adding a suitable acid to provide a compound of formula XI.

41. The process of claim 32 wherein:
(1) Step (a) comprises mixing a solution of R-2-(−)-phenylglycinol with said compound of formula III, and heating the resulting solution at reflux with azeotropic removal of water to provide the imine compound of Formula VI;
(2) Step (b) comprises mixing an acid and a silylating reagent with the compound of formula VI from step (a), and heating the solution at reflux to provide a protected imine compound of formula VII;
(3) The organometallic reagent, in step (c), is in a suitable solvent, and said organometallic reagent is selected from the group consisting of: diethyl zinc, ethylzinc bromide, ethylzinc chloride, ethylmagnesium bromide, ethylmagnesium chloride and ethylithium;
(4) Step (d) comprises deprotecting the imine compound of formula VIII from step (c) with an acid, followed by treatment with a base to form said compound of formula IX;
(5) Step (e) comprises dissolving the compound of formula IX in a suitable solvent, adding $R^4NH_2$, and, following the addition of said $R^4NH_2$, adding an additional agent selected from the group consisting of: $NaIO_4$, $Pb(OAc)_4$, $H_5IO_6$, and mixtures thereof, wherein $R^4$ is selected from the group consisting of alkyl, cycloalkyl, heterocycloalkyl, aryl, heteroaryl, and aralkyl, to provide the intermediate compound of formula X; and
(6) Step (f) comprises (1) dissolving said intermediate compound of formula X from step (e) in a suitable solvent, and (2) adding a suitable acid to provide a compound of formula XI.

42. The process of claim 41 wherein:
(1) said acid in step (b) is selected from the group consisting of: ammonium sulphate, ammonium nitrate, ammonium chloride, $H_2SO_4$, HCl, $H_3PO_4$, citric acid, mesylchloride, paratoluenesulfonic acid, paratoluenesulfonic acid pyridium salt, alkylsulfonic acid, and mixtures thereof;
(2) said silylating reagent in step (b) is selected from the group consisting of: hexamethyldisilazane, TMS chloride, and TMSOTF, wherein said TMS chloride is used in combination with triethylamine, and said TMSOTF is used in combination with triethylamine;

(3) said suitable solvent in step (c) is selected from the group consisting of: benzene, toluene, TBME, THF, DME, dimethoxyethane, and mixtures thereof;
(4) said acid in step (d) is selected from the group consisting of: $H_2SO_4$, HCl, $H_3PO_4$, citric acid, ammonium chloride, and mixtures thereof;
(5) said base in step (d) is selected from the group consisting of: ammonium hydroxide, metal hydroxide, metal oxide, metal carbonate, metal bicarbonate, and mixtures thereof, wherein said metal is selected from the group consisting of: lithium, sodium, potassium, rubidium, cesium, beryllium, magnesium, calcium, strontium, barium, aluminum, indium, thallium, titanium, zirconium, cobalt, copper, silver, zinc cadmium, mercury and cerium; and
(6) said acid in step (f) is selected from the group consisting of: sulfonic acids, tartaric acids, $H_2SO_4$, HCl, $H_3PO_4$, HBr, and carboxylic acids, and mixtures thereof.

43. The process of claim 42 wherein:
(1) said R-2-(−)-phenylglycinol in step (a) is at least about 0.01 molar equivalent with respect to said compound of formula III;
(2) said acid in step (b) is at least about 0.2 molar equivalent with respect to the compound of formula VI;
(3) said organometallic reagent in step (c) is from about 0.1 to about 5 molar equivalents with respect to said compound of formula VII; and
(4) said acid in step (d) is paratoluene sulfonic acid.

44. A process for preparing a compound of the formula XIII:

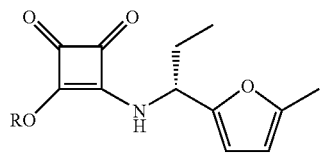

XIII comprising:
(a) converting the compound of formula III

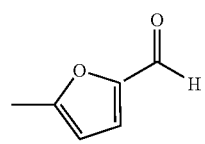

III to a compound of formula VI:

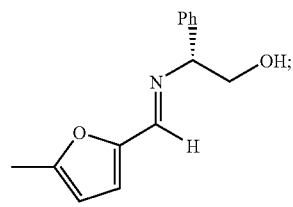

VI (b) adding a protecting group to the compound of formula VI to yield a compound of formula VII:

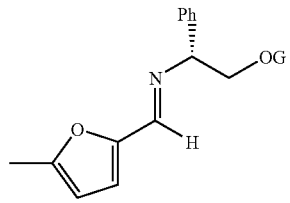

VII wherein G represents a protecting group;
(c) reacting the compound of formula VII with a suitable organometallic reagent, followed by work-up, to yield a compound of formula VIII:

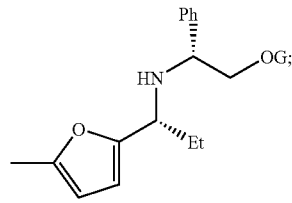

VIII (d) removing the protecting group (G) from the compound of formula VIII to yield a compound of formula IX:

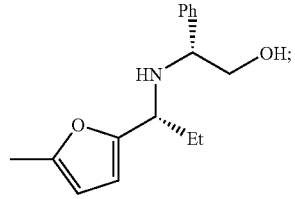

IX (e) converting the compound of formula IX into an imine intermediate compound of formula X:

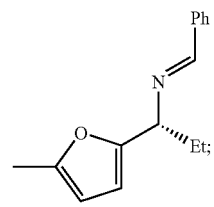

X (f) converting the imine intermediate compound of formula X into the salt of formula XI:

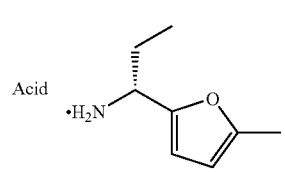

XI and reacting said compound of formula XI with a compound of formula Q:

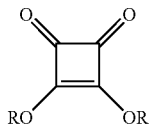

wherein R represents (C$_1$–C$_{10}$)alkyl to produce the compound of formula XIII; or (g) converting the compound of formula XI to the free amine:

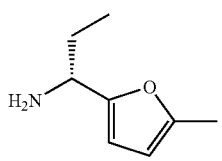

by reacting the compound of formula XI in a suitable solvent with a suitable base, and reacting said compound of formula XII with Q:

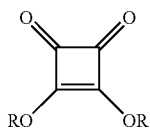

wherein R represents (C$_1$–C$_{10}$)alkyl to produce the compound of formula XIII.

45. The process of claim 44 wherein:
(1) Step (a) comprises mixing a solution of R-2-(−)-phenylglycinol with said compound of formula III, and heating the resulting solution at reflux with azeotropic removal of water to provide the imine compound of Formula VI;
(2) Step (b) comprises mixing an acid and a silylating reagent with the compound of formula VI from step (a), and heating the solution at reflux to provide a protected imine compound of formula VII;
(3) The organometallic reagent, in step (c), is in a suitable solvent, and said organometallic reagent is selected from the group consisting of: diethyl zinc, ethylzinc bromide, ethylzinc chloride, ethylmagnesium bromide, ethylmagnesium chloride and ethyllithium;
(4) Step (d) comprises deprotecting the imine compound of formula VIII from step (c) with an acid, followed by treatment with a base to form said compound of formula IX;
(5) Step (e) comprises dissolving the compound of formula IX in a suitable solvent, adding R$^4$NH$_2$, and, following the addition of said R$^4$NH$_2$, adding an additional agent selected from the group consisting of: NaIO$_4$, Pb(OAc)$_4$, H$_5$IO$_6$, and mixtures thereof, wherein R$^4$ is selected from the group consisting of alkyl, cycloalkyl, heterocycloalkyl, aryl, heteroaryl, and aralkyl, to provide the intermediate compound of formula X;
(6) Step (f) comprises (1) dissolving said intermediate compound of formula X from step (e) in a suitable solvent, and (2) adding a suitable acid to provide a compound of formula XI, and then adding 3,4-dialkoxy-3-cyclobutene-1,2-dione to said compound of formula XI, adjusting the temperature to about 0° C. to about 80° C. to yield a compound of formula XIII;
(7) Step (g) comprises reacting the compound of formula XII, in a suitable solvent with a catalytic amount of a suitable base, with a 3,4-dialkoxy-3-cyclobutene-1,2-dione to yield a compound formula XIII.

46. The process of claim 45 wherein:
(1) said acid in step (b) is selected from the group consisting of: ammonium sulphate, ammonium nitrate, ammonium chloride, H$_2$SO$_4$, HCl, H$_3$PO$_4$, citric acid, mesylchloride, paratoluenesulfonic acid, paratoluenesulfonic acid pyridium salt, alkylsulfonic acid, and mixtures thereof;
(2) said silylating reagent in step (b) is selected from the group consisting of: hexamethyldisilazane, TMS chloride, and TMSOTF, wherein said TMS chloride is used in combination with triethylamine, and said TMSOTF is used in combination with triethylamine;
(3) said suitable solvent in step (c) is selected from the group consisting of: benzene, toluene, TBME, THF, DME, dimethoxyethane, and mixtures thereof;
(4) said acid in step (d) is selected from the group consisting of: H$_2$SO$_4$, HCl, H$_3$PO$_4$, citric acid, ammonium chloride, and mixtures thereof;
(5) said base in step (d) is selected from the group consisting of: ammonium hydroxide, metal hydroxide, metal oxide, metal carbonate, metal bicarbonate, and mixtures thereof, wherein said metal is selected from the group consisting of: lithium, sodium, potassium, rubidium, cesium, beryllium, magnesium, calcium, strontium, barium, aluminum, indium, thallium, titanium, zirconium, cobalt, copper, silver, zinc cadmium, mercury and cerium; and
(6) said acid in step (f) is selected from the group consisting of: sulfonic acids, tartaric acids, H$_2$SO$_4$, HCl, H$_3$PO$_4$, HBr, and carboxylic acids, and mixtures thereof;
(7) said base in step (g) is selected from the group consisting of: pyriding and N(R$^3$)$_3$, wherein each R$^3$ is independently selected from the group consisting of: alkyl, aryl and arylalkyl.

47. The process of claim 46 wherein:
(1) said R-2-(−)-phenylglycinol in step (a) is at least about 0.01 molar equivalent with respect to said compound of formula III;
(2) said acid in step (b) is at least about 0.2 molar equivalent with respect to the compound of formula VI;
(3) said organometallic reagent in step (c) is from about 0.1 to about 5 molar equivalents with respect to said compound of formula VII;
(4) said acid in step (d) is paratoluene sulfonic acid; and
(5) said base in step (g) is diisopropylethylamine.

48. A process for producing a compound of the formula I:

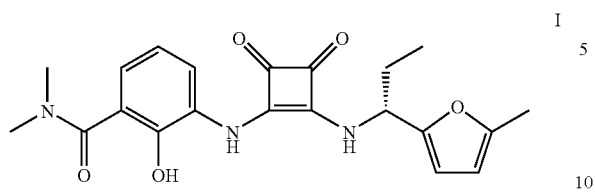

I comprising:
(a) converting the compound of formula III

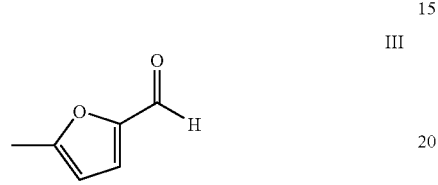

III to a compound of formula VI:

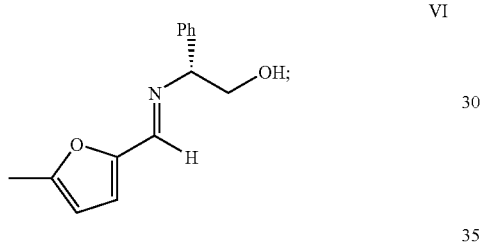

VI (b) adding a protecting group to the compound of formula VI to yield a compound of formula VII:

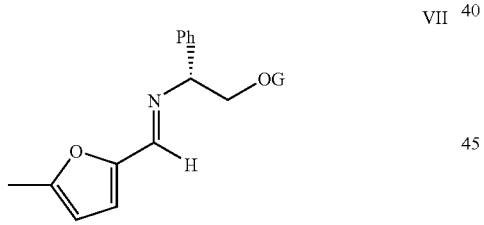

VII wherein G represents a protecting group;
(c) reacting the compound of formula VII with a suitable organometallic reagent, followed by work-up, to yield a compound of formula VIII:

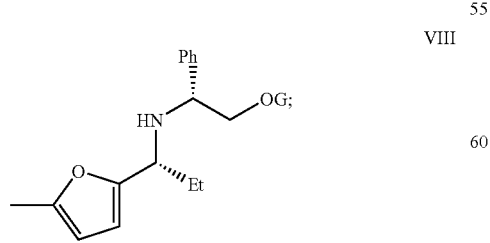

VIII (d) removing the protecting group (G) from the compound of formula VIII to yield a compound of formula IX:

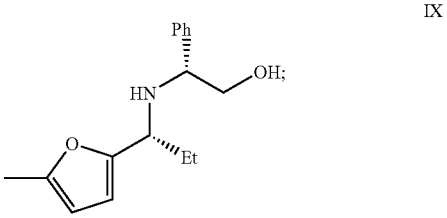

IX (e) converting the compound of formula IX into an imine intermediate compound of formula X:

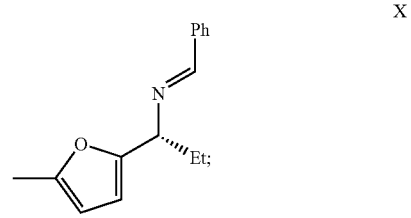

X (f) converting the imine intermediate compound of formula X into the salt of formula XI:

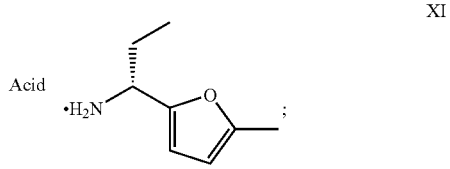

XI (g) reacting the compound of formula XI with the compound of formula Q:

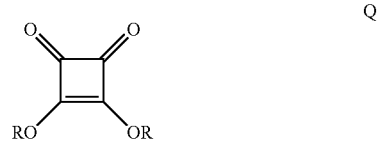

Q to yield a compound of formula XIII:

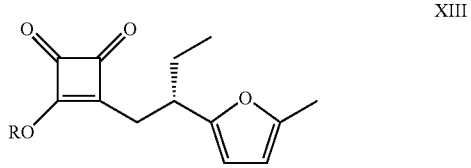

XIII wherein R represents $(C_1-C_{10})$alkyl in formulas Q and XIII; or
(h) converting the compound of formula XI to a compound of formula XII:

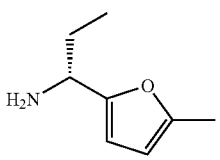

and reacting the compound of formula XII with a compound of formula Q:

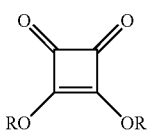

to yield a compound of formula XIII:

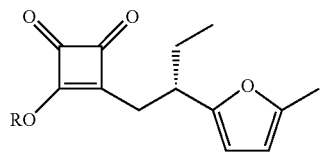

wherein R represents $(C_1-C_{10})$alkyl in formulas Q and XIII;

(i) converting the compound of formula II

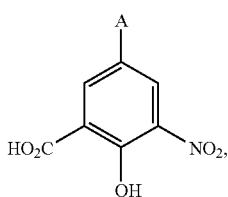

wherein A is selected from the group consisting of Br, Cl and I, to a compound of formula IV:

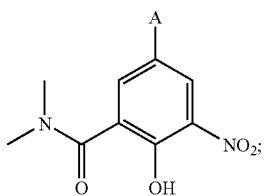

(j) hydrogenating the compound of formula IV with a suitable hydrogenation catalyst under hydrogen pressure, to form the intermediate compound of formula IV(i):

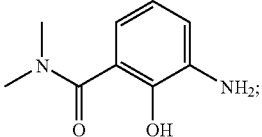

(k) reacting the compound of formula IV(i) with the compound of formula XIII to yield the compound of formula I.

49. The process of claim 48 wherein:
(1) Step (a) comprises mixing a solution of R-2-(–)-phenylglycinol with said compound of formula III, and heating the resulting solution at reflux with azeotropic removal of water to provide the imine compound of Formula VI;
(2) Step (b) comprises mixing an acid and a silylating reagent with the compound of formula VI from step (a), and heating the solution at reflux to provide a protected imine compound of formula VII;
(3) The organometallic reagent, in step (c), is in a suitable solvent, and said organometallic reagent is selected from the group consisting of: diethyl zinc, ethylzinc bromide, ethylzinc chloride, ethylmagnesium bromide, ethylmagnesium chloride and ethyllithium;
(4) Step (d) comprises deprotecting the imine compound of formula VIII from step (c) with an acid, followed by treatment with a base to form said compound of formula IX;
(5) Step (e) comprises dissolving the compound of formula IX in a suitable solvent, adding $R^4NH_2$, and, following the addition of said $R^4NH_2$, adding an additional agent selected from the group consisting of: $NaIO_4$, $Pb(OAc)_4$, $H_5IO_6$, and mixtures thereof, wherein $R^4$ is selected from the group consisting of alkyl, cycloalkyl, heterocycloalkyl, aryl, heteroaryl, and aralkyl, to provide the intermediate compound of formula X;
(6) Step (f) comprises (1) dissolving said intermediate compound of formula X from step (e) in a suitable solvent, and (2) adding a suitable acid to provide a compound of formula XI, and then adding 3,4-dialkoxy-3-cyclobutene-1,2-dione to said compound of formula XI, adjusting the temperature to about 0° C. to about 80° C. to yield a compound of formula XIII;
(7) Step (g) comprises reacting the compound of formula XII, in a suitable solvent with a catalytic amount of a suitable base, with a 3,4-dialkoxy-3-cyclobutene-1,2-dione to yield a compound formula XIII;
(8) Substituent A is Br in step (i);
(9) Step (i) comprises reacting said compound of formula II with a suitable acid chloride in a suitable solvent at a suitable temperature, and then reacting the resulting reactionmixture with dimethylamine;
(10) step (j) comprises making a mixture of said compound of formula IV, a hydrogenation catalyst, and a suitable base, and pressurizing the mixture under $H_2$ pressure;
(11) Step (k) comprises reacting the compound of formula XIII with the compound of formula IV(i) at a suitable temperature to yield the compound of formula I.

50. The process of claim 49 wherein:
(1) said acid in step (b) is selected from the group consisting of: ammonium sulphate, ammonium nitrate, ammonium chloride, H₂SO₄, HCl, H₃PO₄, citric acid, mesylchloride, paratoluenesulfonic acid, paratoluenesulfonic acid pyridium salt, alkylsulfonic acid, and mixtures thereof;

(2) said silylating reagent in step (b) is selected from the group consisting of: hexamethyldisilazane, TMS chloride, and TMSOTF, wherein said TMS chloride is used in combination with triethylamine, and said TMSOTF is used in combination with triethylamine;

(3) said organometallic reagent in step (c) is in a suitable solvent, said organometallic reagent is selected from the group consisting of: diethyl zinc, ethylzinc bromide, ethylzinc chloride, ethylmagnesium bromide, ethylmagnesium chloride and ethyllithium, and said suitable solvent in step (c) is selected from the group consisting of: benzene, toluene, TBME, THF, DME, dimethoxyethane, and mixtures thereof;

(4) said acid in step (d) is selected from the group consisting of: H₂SO₄, HCl, H₃PO₄, citric acid, ammonium chloride, and mixtures thereof;

(5) said base in step (d) is selected from the group consisting of: ammonium hydroxide, metal hydroxide, metal oxide, metal carbonate, metal bicarbonate, and mixtures thereof, wherein said metal is selected from the group consisting of: lithium, sodium, potassium, rubidium, cesium, beryllium, magnesium, calcium, strontium, barium, aluminum, indium, thallium, titanium, zirconium, cobalt, copper, silver, zinc cadmium, mercury and cerium; and (6) said acid in step (f) is selected from the group consisting of: sulfonic acids, tartaric acids, H₂SO₄, HCl, H₃PO₄, HBr, and carboxylic acids, and mixtures thereof;

(7) said solvent used with said acid chloride in step (i) is selected from the group consisting of: acetonitrile, THF, t-butylmethylether, methylenechloride, toluene, ethylacetate, diethylether, and chloroform;

(8) said acid chloride in step (i) is selected from the group consisting of: thionyl chloride and oxalyl chloride;

(9) said dimethylamine in step (i) is dimethylamine gas or a solution of dimethylamine wherein the solvent used in said dimethylamine solution is selected from the group consisting of: acetonitrile, THF, t-butylmethylether, methylenechloride, toluene, ethylacetate, diethylether, and chloroform;

(10) a suitable base is used in step (j) and said base is selected from the group consisting of: KOH, NaOH, Na₂CO₃, K₂CO₃, NaHCO₃, KHCO₃, tetramethylguanidine, DBU, diisopropylethylamine and mixtures thereof; and

(11) said hydrogenation catalyst in step (j) is selected from the group consisting of: Pd/C, Pt/C, PdOH, and raney nickel.

51. The process of claim 50 wherein:

(1) said R-2-(-)-phenylglycinol in step (a) is at least about 0.01 molar equivalent with respect to said compound of formula III;

(2) said acid in step (b) is at least about 0.2 molar equivalent with respect to the compound of formula VI;

(3) said organometallic reagent in step (c) is from about 0.1 to about 5 molar equivalents with respect to said compound of formula VII;

(4) said acid in step (d) is paratoluene sulfonic acid;

(5) said acid chloride in step (i) is thionyl chloride;

(5) said solvent used with said acid chloride in step (i) is acetonitrile;

(7) said dimethlyamine in step (i) is at a concentration of at least 1 molar equivalent with respect to said compound of formula II;

(8) said hydrogenation catalyst in step (j) is Pd/C; and (9) said H₂ pressure in step (j) is from about 10 to about 500 psi.

52. A process for preparing a compound of formula I:

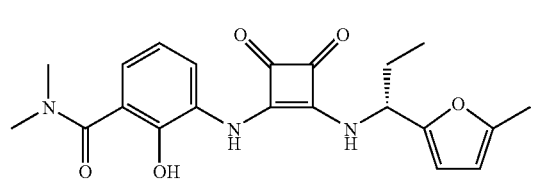

comprising:
(a) dissolving the compound of formula II:

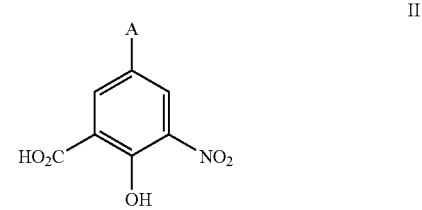

in:
a solvent selected from the group consisting of: acetonitrile, THF, t-butylmethylether, methylenechloride, toluene, ethylacetate, diethylether, and chloroform, and an acid chloride selected from the group consisting of: thionyl chloride and oxalyl chloride, wherein a catalytic amount of DMF is optionally used when oxalyl chloride is used;

and adjusting the temperature of the resulting reaction mixture to a about −20° C. to about 110° C.;

cooling the reaction mixture, when the reaction is complete, to a temperature of about 5° C. to about 10° C.;

adding dimethylamine gas or a solution of dimethylamine, at a concentration of at least about 1 molar equivalent with respect to the compound of formula II, wherein the solvent used in said dimethylamine is selected from the group consisting of: acetonitrile, THF, t-butylmethylether, methylenechloride, toluene, ethylacetate, diethylether, and chloroform;

adjusting the temperature of the resulting reaction mixture to a temperature of about −20° C. to about 50° C.;

acidifying the resulting reaction mixture with an aqueous acid to a pH of about 0 to about 7, to produce a compound of formula IV:

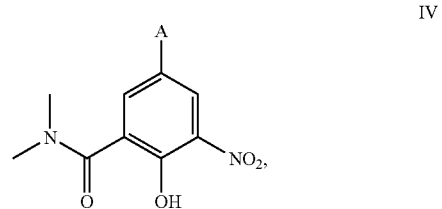

wherein A is in the compounds of formulas II and IV is selected from the group consisting of: Br, Cl and I;

(b) hydrogenating the compound of formula IV by mixing said compound of formula IV with:

a base selected from the group consisting of: KOH, NaOH, Na₂CO₃, K₂CO₃, NaHCO₃, KHCO₃, tetramethylguanidine, DBU, diisopropylethylamine and mixtures thereof, wherein said base is in a concentration of at least about 1 molar equivalent with respect to the compound of formula IV, a hydrogenation catalyst selected from the group consisting of: Pd/C, Pt/C, PdOH, and Raney nickel; and a solvent selected from the group consisting of: THF, methanol, ethanol, propanol, isopropanol, acetonitrile, ethyl acetate, and mixtures thereof; and pressurizing the resulting mixture under hydrogen at a pressure of about 10 to about 500 psi to produce the intermediate compound of formula IV(i):

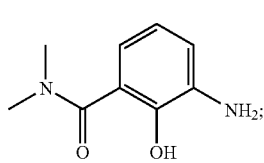

(c) adding the compound of formula Q:

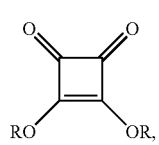

in a concentration of at least 1 molar equivalent with respect to the compound of formula IV(i), to the reaction mixture comprising the compound of formula IV(i) obtained in step (b), and adjusting the temperature to about 0° C. to about 80° C. to produce a compound of formula V:

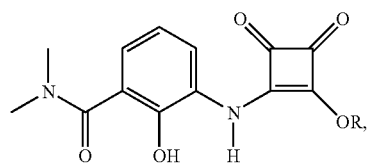

wherein R in said compound of formula Q is selected from the group consisting of: methyl, ethyl, propyl and isopropyl, and wherein said reaction is optionally catalyzed by a base selected from the group consisting of: KOH, NaOH, Na₂CO₃, K₂CO₃, K₂CO₃, NaHCO₃, KHCO₃, tetramethylguanidine, DBU, diisopropylethylamine, and mixtures thereof;

(d1) mixing: the compound of formula V from step (c) with the compound of formula XI

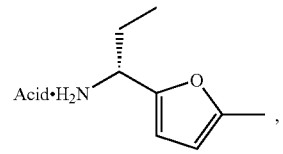

and a base in a solvent, heating the resulting reaction mixture to a temperature of about 20° C. to about 150° C., and then acidifying the reaction mixture to a pH of about 3 to about 7, to produce a compound of formula I; said base being selected from the group consisting of: pyridine, dimethylaminopyridine (DMAP), diisopropylethylamine and —N(R²)₃; wherein each R² is independently selected from the group consisting of: alkyl and cycloalkyl; and said base being used in a concentration of at least about 1 molar equivalent with respect to the compound of formula IV; and said solvent being selected from the group consisting of: nitrile, ether, and alcohol solvents; or (d2) mixing the compound of formula XI:

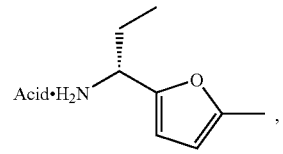

with water and solvent selected from the group consisting of: ethers and methylene chloride;

basifying the resulting reaction mixture in a base selected from the group consisting of: NaOH, KOH, Mg(OH)₂, Na₂CO₃ and K₂CO₃, to a pH of about 7 to about 14, said basification being done at a temperature of about 0° C. to about 50° C. to produce a compound of formula XII:

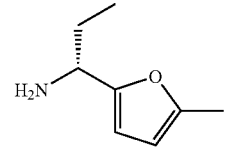

dissolving said compound of formula V from step (c) in a solvent selected from the group consisting of: alcohol solvents, nitrile solvents, ether solvents and toluene;

mixing the resulting solution with the compound of formula XII, and optionally adding a catalytic amount of a base to the resulting solution, wherein said base is selected from the group consisting of: pyridine and —N(R³)₃, wherein R³ is selected from the group consisting of: alkyl, aryl, aralkyl, and arylalkyl, and wherein the temperature of the resulting solution is about 10° C. to about 150° C., to produce a compound of formula I;

(e) wherein said compound of formula XI is prepared by: mixing the compound of formula III:

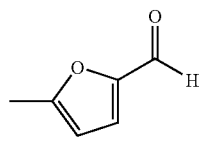

III with 0.01 molar equivalent, with respect to the compound of formula III, of R-2-(−)-phenylglycinol in a solvent selected from the group consisting of: aromatic solvents, halogenated solvents, alcohol solvents, nitrile solvents, ether solvents, and mixtures thereof, and heating the resulting mixture at reflux to produce a compound of formula VI:

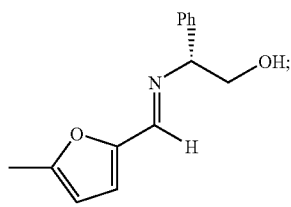

VI mixing the solution comprising the compound of formula VI with a silylating reagent selected from the group consisting of: hexamethyldisilazane, TMS chloride, and TMSOTF, wherein the TMS chloride or TMSOTF is used in combination with an aryl or alkyl base, and an acid in a concentration of at least about 0.2 molar equivalent with respect to the compound of formula VI, said acid being selected from the group consisting of: ammonium sulphate, ammonium nitrate, ammonium chloride, $H_2SO_4$, HCl, $H_3PO_4$, citric acid, mesyl chloride, paratoluenesulfonic acid, paratoluenesulfonic acid pyridinium salt, and alkylsulfonic acid, and heating the resulting reaction mixture at reflux to produce an imine compound of formula VII:

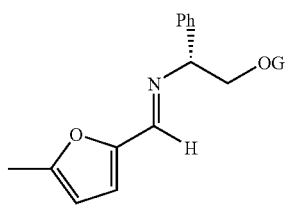

VII wherein G represents a protecting group that is the silylating reagent used;

mixing said imine compound of formula VII with an organometallic reagent in a solvent at a temperature of about 0° C. to about 80° C., said organometallic reagent being selected from the group consisting of: diethyl zinc, ethylzinc bromide, ethylzinc chloride, ethylmagnesium bromide, ethylmagnesium chloride and ethyllithium, said organometallic reagent being used in a concentration of 0.1 to about 5 molar equivalents with respect to the compound of formula VII, said solvent being selected from the group consisting of: benzene, toluene, TBME, THF, DME, dimethoxyethane, and mixtures thereof, to produce a compound of formula VIII:

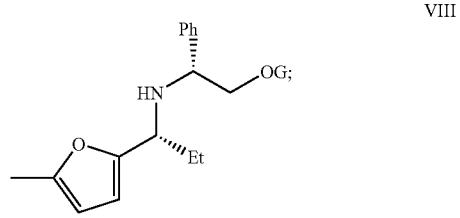

VIII adding the compound of formula VIII to a cooled aqueous acid, said acid being at a concentration of about 2.5 to about 5 molar equivalents with respect to the compound of formula VIII, adding water and a cosolvent and mixing the resulting mixture, adding a base to said mixture to adjust the pH of the aqueous phase to about 9 to about 13, to produce a compound of formula IX:

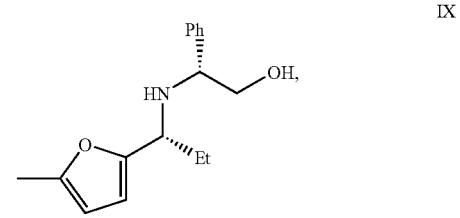

IX said co-solvent being selected from the group consisting of: methanol, ethanol, propanol, isopropanol, butanol, sec-butanol, pentanol, hexanol, heptanol, octanol, and mixtures thereof, said base being selected from the group consisting of: ammonium hydroxide, metal hydroxide, metal oxide, metal carbonate, metal bicarbonate, and mixtures thereof, wherein said metal is selected from the group consisting of: lithium, sodium, potassium, rubidium, cesium, beryllium, magnesium, calcium, strontium, barium, aluminum, indium, thallium, titanium, zirconium, cobalt, copper, silver, zinc cadmium, mercury and cerium, or said base being selected from the group consisting of: a metal salt of a $(C_1-C_{12})$alkanol and a $(C_3-C_{12})$cycloalkanol, wherein the metal is selected from the group consisting of: Li, Na, K, and Mg;

dissolving the compound of formula IX in solvent selected from the group consisting of: water, methanol, ethanol, propanol, isopropanol, butanol, sec-butanol, pentanol, hexanol, tetrahydrofuran, 1,2-dimethoxyethane, 1,2-diethoxymethane, diglyme, 1,4-dioxane, and mixtures thereof, cooling the resulting solution to a temperature of about −5° C. to about 20° C., adding $R^4NH_2$ to said solution, and then adding an agent selected from the group consisting of: $NaIO_4$, $Pb(OAc)_4$, $H_5IO_6$, and mixtures thereof, to produce a compound of X:

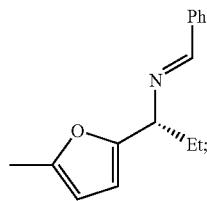

and wherein $R^4$ is selected from the group consisting of alkyl, cycloalkyl, heterocycloalkyl, aryl, heteroaryl, and aralkyl;

dissolving the compound of formula X in a solvent and adding the resulting solution to an acid solution at a temperature ranging preferably from about −50° C. to about 80° C. to produce the compound of formula XI:

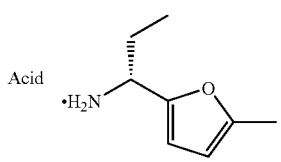

said compound XI being a salt, wherein said solvent is selected from the group consisting of: hydrocarbon solvents and ethers and mixtures thereof, and said acid is selected from the group consisting of: sulfonic acids, tartaric acids, $H_2SO_4$, HCl, $H_3PO_4$, HBr, carboxylic acids and mixtures thereof.

53. The process of claim 52 wherein:

in step (a), the preparation of the compound of formula IV, the reaction the reaction mixture of said compound of formula II and said acid chloride is 40° C. to about 90° C., said dimethylamine is at a concentration of at least about 2 molar equivalents with respect to the compound of formula II, said temperature of said reaction mixture is about 0° C. to about 25° C., said reaction mixture is acidified to a pH of about 1 to about 5, said acid for said aqueous acid is selected from the group consisting of: HCl, $H_2SO_4$, $H_3PO_4$, and mixtures thereof;

in step (b), the hydrogenation of the compound of formula IV, said base is selected from the group consisting of: $Na_2CO_3$, $K_2CO_3$, and mixtures thereof, said base is used at a concentration of about 1.05 to about 1.5 molar equivalents, said catalyst is selected from the group consisting of Pd/C and PdOH, said solvent is selected from the group consisting of: methanol, ethanol, propanol, isopropanol, and mixtures thereof, and said hydrogen pressure is about 20 to about 200 psi;

in step (c), the reaction of the compound of formula Q with the compound of formula IV(i), the compound of formula Q is used at a concentration of about 1 to about 2 molar equivalents, said temperature is about 20° C. to about 50° C., and said optional base is selected from the group consisting of: $Na_2CO_3$, $K_2CO_3$ and mixtures thereof;

in step (d1), the reaction of the compound of formula V with the compound of formula XI, said base is used in an amount of about 1 to about 2 molar equivalents with respect to the compound of formula V, said solvent is selected from the group consisting of alcohol and nitrile solvents, said temperature is about 40° C. to about 80° C., and said pH is about 3 to about 5;

in step (d2), the reaction of the compound of formula V with the compound of formula XII:

said mixture with said compound of formula XI is basified with NaOH or KOH to a pH of about 10 to about 14 at a temperature of about 10° C. to about 40° C. to produce said compound of formula XII, said compound of formula V is dissolved in an alcohol solvent, said compound of formula XII being used at a concentration about 1 molar equivalent with respect to the compound of formula V, said catalytic base being selected from the group consisting of: pyridine and $—N(R^3)_3$ wherein each $R^3$ is independently selected from the group consisting of ethyl, isopropyl, propyl, butyl, phenyl, tolyl and benzyl, and said temperature of said resulting solution with the compound of formula XII being about 40° C. to about 80° C.;

in step (e), in the reaction to produce the compound of formula VI from the compound of formula III, said R-2-(−)-phenylglycinol is in a concentration of about 0.5 to about 1.5 molar equivalents, and said solvent for said R-2-(−)-phenylglycinol is selected from the group consisting of: benzene, toluene, dichloromethane, methylene chloride, chlorobenzene, methanol, ethanol, propanol, isopropanol, n-propanol, butanol, acetonitrile, THF and t-butylmethylether;

in step (e) in the reaction to produce the compound of formula VII from the compound of formula VI, said silylating reagent is selected from the group consisting of: hexamethyldisilazane, TMS chloride, and TMSOTF, wherein the TMS chloride or TMSOTF is used in combination with triethylamine, and said acid is selected from the group consisting of: ammonium sulphate, ammonium nitrate and ammonium chloride, said acid at a concentration of at least about 0.4 molar equivalents with respect to the compound of formula VI;

in step (e), in the reaction to produce the compound of formula VIII from the compound of formula VII, said organometallic reagent is used in a concentration of about 1 to about 5 molar equivalents with respect to the compound of formula VII, said solvent is selected from the group consisting of: THF, TBME, and mixtures thereof, and said temperature is about 10° C. to about 50° C.;

in step (e), in the reaction to produce the compound of formula IX from the compound of formula VIII, said cooled aqueous acid is at a temperature of about 0° C. to about 15° C., said acid is selected from the group consisting of: $H_2SO_4$, HCl, $H_3PO_4$, and mixtures thereof, said acid is in a concentration of about 2.5 to about 3 molar equivalents with respect to the compound of formula VIII, said cosolvent is selected from the group consisting of: methanol, ethanol, propanol, isopropanol, butanol, sec-butanol, pentanol, hexanol, heptanol, octanol, and mixtures thereof, said base is selected from the group consisting of: KOH, NaOH, NH₄OH, LiOH and CsOH, and said pH is adjusted to about 10 to about 11, in step (e), in the reaction to produce the compound of formula X from the compound of formula IX, the resulting solution is cooled to about 0° C. to about 15° C., and said R⁴ is a (C₁–C₃)alkyl; and in step (e), in the reaction to produce the compound of formula XI from the compound of formula X, said compound of formula XI is dissolved in a solvent selected from the group consisting of: toluene, xylene, chlorobenzene, dichlorobenzene, diethyl ether, dipropyl ether and dibutyl ether, 1,2-dimethoxyethane, 1,2-diethoxyethane, diglyme, 1,4-dioxane, tetrahydrofuran and mixtures thereof, said acid in said acid solution is selected from the group consisting of: paratoluene sulfonic acid and alkylsulfonic acids, and said temperature is about −20° C. to about 20° C.

54. The process of claim 53 wherein:

in step (a), the preparation of the compound of formula IV, said compound of formula II is dissolved in acetonitrile and thionyl chloride, said temperature is about 65° C. to about 75° C., said dimethylamine is dissolved in acetonitrile, said dimethylamine being at a concentration of about 2.5 molar equivalents with respect to the compound of formula II, said temperature of said reaction mixture is about 5° C. to about 10° C., said reaction mixture is acidified to a pH of about 2 to about 3, said aqueous acid is H₂SO₄, and said substituent A is Br;

in step (b), the hydrogenation of the compound of formula IV, said base is K₂CO₃ used at a concentration of about 1.05 to about 1.1 molar equivalents, said catalyst is Pd/C, said solvent is ethanol, and said hydrogen pressure is about 100 to about 120 psi;

in step (c), the reaction of the compound of formula Q with the compound of formula IV(i), the compound of formula Q is used at a concentration of about 1.3 to about 1.5 molar equivalents, said temperature is about 25° C. to about 35° C., R is ethyl, and said optional base is K₂CO₃;

in step (d1), the reaction of the compound of formula V with the compound of formula XI, the compound of formula XI is used in an amount of about 1.1 molar equivalents, said base is triethylamine used in an amount of about 1.3 to about 1.5 molar equivalents with respect to the compound of formula V, said solvent is acetonitrile, said temperature is about 60° C. to about 70° C., and said pH is about 4;

in step (d2), the reaction of the compound of formula V with the compound of formula XII, said solvent used with said compound of formula XI is t-butyl methyl ether, said mixture with said compound of formula XI is basified with NaOH to a pH of about 12.5 to about 13.5 at a temperature of about 20° C. to about 30° C. to produce said compound of formula XII, said compound of formula V is dissolved in the solvent n-propanol, said compound of formula XII being used at a concentration about 1.1 molar equivalents with respect to the compound of formula V, said catalytic base being diisopropylethylamine, said temperature of said resulting solution with the compound of formula XII being about 60° C. to about 70° C.

in step (e), in the reaction to produce the compound of formula VI from the compound of formula III, said R-2-(−)-phenylglycinol is in a concentration of about 0.9 to about 1.1 molar equivalents, and said solvent for said R-2-(−)-phenylglycinol is THF;

in step (e) in the reaction to produce the compound of formula VII from the compound of formula VI, said silylating reagent is hexamethyldisilazane, and said acid is ammonium sulphate at a concentration of at least about 0.5 molar equivalents with respect to the compound of formula VI;

in step (e), in the reaction to produce the compound of formula VIII from the compound of formula VII, said organometallic reagent is ethylmagnesium bromide used in a concentration of about 2 to about 3 molar equivalents with respect to the compound of formula VII, said solvent is TBME, and said temperature is about 20° C. to about 35° C.;

in step (e), in the reaction to produce the compound of formula IX from the compound of formula VII, said cooled aqueous acid is at a temperature of about 0° C. to about 10° C., said acid is H₂SO₄, said acid is in a concentration of about 2.5 molar equivalents with respect to the compound of formula VIII, said cosolvent is sec-butanol, said base is NH₄OH, and said pH is adjusted to about 11, in step (e), in the reaction to produce the compound of formula X from the compound of formula IX, said compound of formula IX is dissolved in ethanol and the resulting solution is cooled to about 0° C. to about 10° C., said R⁴ is methyl, and said agent is NaIO₄; and in step (e), in the reaction to produce the compound of formula XI from the compound of formula X, said compound of formula XI is dissolved in THF, said acid in said acid solution is paratoluene sulfonic acid, and said temperature is about 0° C. to about 10° C.

55. A compound of the formula:

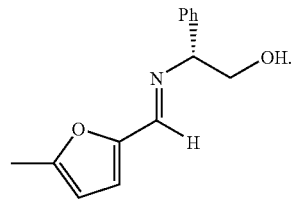

56. A compound of the formula:

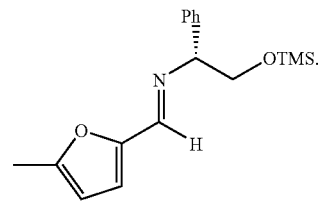

57. A compound of the formula:

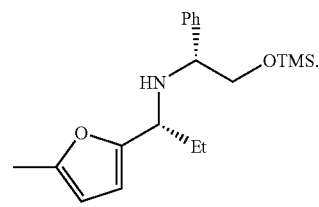

58. A compound of the formula:
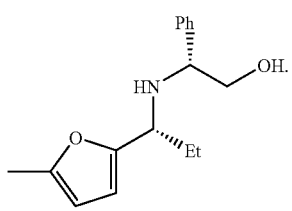
59. A compound of the formula:
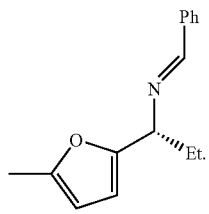
* * * * *